(12) United States Patent
DiAngelo et al.

(10) Patent No.: US 9,480,593 B2
(45) Date of Patent: Nov. 1, 2016

(54) DISTRACTION AND MOBILITY BACK SUPPORT

(71) Applicant: University of Tennessee Research Foundation, Memphis, TN (US)

(72) Inventors: Denis J. DiAngelo, Germantown, TN (US); John Simmons, Germantown, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 422 days.

(21) Appl. No.: 14/209,925

(22) Filed: Mar. 13, 2014

(65) Prior Publication Data

US 2014/0276308 A1   Sep. 18, 2014

Related U.S. Application Data

(60) Provisional application No. 61/798,960, filed on Mar. 15, 2013.

(51) Int. Cl.
*A61F 5/00*   (2006.01)
*A61F 5/02*   (2006.01)
*A61F 5/03*   (2006.01)

(52) U.S. Cl.
CPC .. *A61F 5/02* (2013.01); *A61F 5/03* (2013.01)

(58) Field of Classification Search
CPC ...... A61F 5/028; A61F 5/0102; A61F 5/026; A61F 5/0193; A61F 5/02; A61F 5/024; A61F 5/30; A61F 2002/7862; A61F 2005/0132; A61F 2005/0134; A61F 2005/0155; A61F 2005/0172; A61F 2005/0179; A61F 5/055; A61F 13/085; A61F 13/00987; A61F 13/00995; A61F 13/08; A61F 13/145; A61F 13/148
USPC ................... 602/19; 128/874–875
See application file for complete search history.

(56) References Cited

U.S. PATENT DOCUMENTS

| | | |
|---|---|---|
| 2,813,526 A | 11/1957 | Beebe |
| 3,667,457 A | 6/1972 | Zumaglini |
| 3,827,429 A | 8/1974 | Heikes |
| 3,945,376 A | 3/1976 | Kuehnegger |
| 4,230,101 A | 10/1980 | Gold |
| RE31,564 E | 4/1984 | Hendricks |
| 4,688,558 A | 8/1987 | Hooper, Jr. et al. |
| 4,691,696 A * | 9/1987 | Farfan de los Godos ............ A61F 5/028 128/95.1 |
| 4,715,362 A | 12/1987 | Scott |
| 4,721,102 A | 1/1988 | Pethybridge |
| 4,907,575 A | 3/1990 | Satterthwaite |
| 4,930,499 A | 6/1990 | Rowe |
| 5,158,531 A | 10/1992 | Zamosky |

(Continued)

*Primary Examiner* — Michael Brown
(74) *Attorney, Agent, or Firm* — Peter L. Brewer; Baker Donelson IP Group

(57) ABSTRACT

A back support device is provided herein. The device is configured to support a portion of a burden or load that would otherwise be borne by a user's spinal column and abdomen. The device includes an upper component that is dimensioned to be worn around the torso of the user, and a lower component that is dimensioned to be worn around the user's hips and waistline. The device further comprises a plurality of medial elements. Each medial element is operatively connected to the upper and lower components so that each medial element may support a portion of the burden, thereby transferring the burden from the upper component to the lower component. The medial elements provide support and simultaneous freedom of movement by providing a lifting distraction support upon the spinal column and abdomen.

34 Claims, 30 Drawing Sheets

(56) References Cited

U.S. PATENT DOCUMENTS

| | | | |
|---|---|---|---|
| 5,437,617 A | 8/1995 | Heinz et al. | |
| 5,462,518 A | 10/1995 | Hatley et al. | |
| 5,547,462 A | 8/1996 | Lanigan et al. | |
| 5,549,534 A | 8/1996 | Parvioinen | |
| 5,667,461 A | 9/1997 | Hall | |
| 5,718,670 A | 2/1998 | Bremer | |
| 5,797,955 A | 8/1998 | Walters | |
| 5,950,628 A | 9/1999 | Dunfee | |
| 6,267,741 B1 * | 7/2001 | Lerman | A61F 5/055 128/DIG. 23 |
| 6,280,405 B1 | 8/2001 | Broselid | |
| 6,302,859 B1 | 10/2001 | Cushman | |
| 6,540,707 B1 | 4/2003 | Stark et al. | |
| 6,776,767 B2 | 8/2004 | Reinecke et al. | |
| 7,070,572 B2 | 7/2006 | Reinecke et al. | |
| 7,074,201 B2 | 7/2006 | Reinecke et al. | |
| 7,276,038 B2 | 10/2007 | Reinecke et al. | |
| 7,445,608 B2 | 11/2008 | Dunfee et al. | |
| 8,066,654 B2 | 11/2011 | Sandifer et al. | |
| 8,308,670 B2 | 11/2012 | Sandifer et al. | |
| 8,758,284 B1 * | 6/2014 | Kozersky | A61F 5/026 602/19 |
| 2003/0181839 A1 * | 9/2003 | Bremer | A61F 5/055 602/19 |
| 2006/0161083 A1 | 7/2006 | Duntee et al. | |
| 2011/0105971 A1 * | 5/2011 | Ingimundarson | A61F 5/024 602/19 |
| 2011/0184325 A1 | 7/2011 | Behzadian et al. | |
| 2014/0039371 A1 | 2/2014 | Johnson et al. | |

* cited by examiner

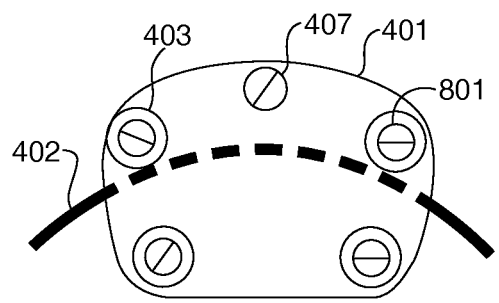
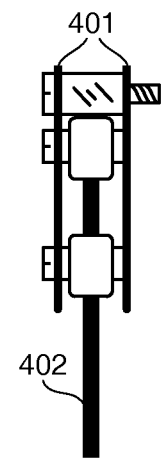
FIG. 9A
FIG. 9B
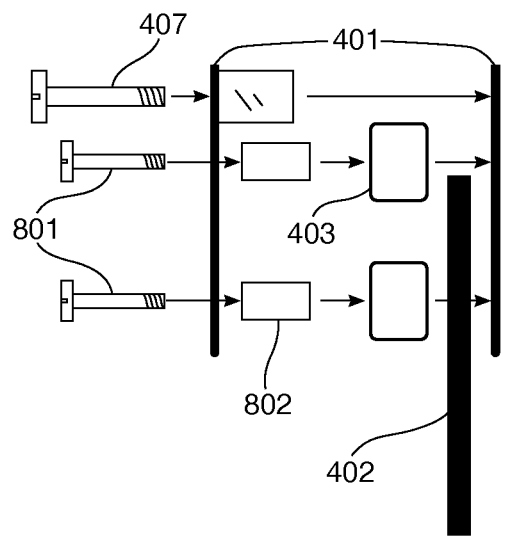
FIG. 9C

DISTRACTION AND MOBILITY BACK SUPPORT

CROSS REFERENCE TO RELATED APPLICATIONS

This application claims the benefit of U.S. Ser. No. 61/798,960 filed Mar. 15, 2013. That application is entitled "Lifting Distraction Back Support Device." The provisional application is referred to and incorporated herein by reference in its entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

BACKGROUND OF THE INVENTION

This section is intended to introduce various aspects of the art, which may be associated with selected embodiments of the present disclosure. This discussion is believed to assist in providing a framework to facilitate a better understanding of particular aspects of the present disclosure. Accordingly, it should be understood that this section should be read in this light, and not necessarily as admissions of prior art.

FIELD OF THE INVENTION

The present disclosure relates generally to back support devices. More particularly, the present disclosure relates to back support devices providing a built-in lift structure for comfortably lifting the torso of a user and supporting the spinal column without significantly impeding user mobility.

DISCUSSION OF TECHNOLOGY

Back pain is a ubiquitous problem among the adult population in the United States. Back pain reportedly affects approximately 80 percent of adults in the U.S. and costs more than $100 billion each year.

For many of these individuals, surgery is not a viable solution. This may be due to cost, or lack of insurance. Alternatively, this may be due to a lack of available downtime or family support. Alternatively still, this may be because surgery is not considered to be efficacious by the treating orthopedic specialist.

Many of the four out of five Americans with back pain are able to receive temporal relief and expanded range-capacity (partially resulting from reduced pain at range boundaries) through water exercise. Such exercise may be active, or may involve just walking and standing in water. This benefit may occur even when the patient is only partially submerged. As the water displaces the load around the painful spine, the patient enjoys a period of relief from spinal pain while also being able to exercise with uncharacteristic motion freedom. Unfortunately, water therapy is not available to all individuals. Even when it is available, water therapy may offer only temporal relief for some individuals.

Another option frequently employed by adults suffering from back pain is to wear a so-called back brace, or orthosis. Various back braces are available on the market. These braces generally seek to provide spinal stabilization via protective immobilization and/or decompression and load sharing.

In some designs, these back braces use a mostly rigid, formed plastic to provide a level of comfort and support. This creates a degree of immobilization, lessening pain induced by nerve root impingement or myofascial insult. Other back braces use straps, buckles, cinches, or ratchet-winches to make the orthotic device tight around the user's torso. This too helps to relieve pressure from the spine by distributing the load. A concern from such devices is that the brace is often too tight to be left on long enough to permit full healing, or even extended relief. In any instance, the above back brace designs limit user mobility.

Various patents have issued, and a number of patent applications have published, disclosing back support devices that seek to relieve axial load on the spine. These devices typically apply a squeezing force on the body of the user. This squeezing force is generally applied to the mid and/or lower sections of the torso, thereby creating a slight elevating effect.

One example of such a patent is U.S. Pat. No. 5,718,670, issued to Bremer. This patent is entitled "Thoracal Lumbosacral Orthosis for a Human Torso." The '670 patent discloses a device having front and back panels, with attachments on the opposing sides. The attachments effectively "sandwich" the user, providing both immobilization and pressure support in desired directions. Of interest, the posterior panel has an opening overlying the spine of the patient. This posterior opening is closed with a flexible material (such as foam), such that only light pressure is applied to a spinal surgical site in response to attempted movements by the patient.

U.S. Pat. No. 5,547,462, issued to Lanigan, et al, goes beyond the simple corset by offering an angled front abdomen panel. This patent is entitled "Back Brace." According to the '462 patent, when the orthotic device is tightened around the user, the corset exerts a slightly angled force that, rather than simply squeezing in, also squeezes up on the lower stomach. This stomach elevation may have some benefit as it indirectly offloads a degree of pressure to the spine. However, the other side of the device offsets this force with medial pressure to the other side of the spine at a slightly downward angle.

U.S. Pat. Publ. No. 2006/0161083, entitled "Ambulatory Spinal Unloading Method and Apparatus," describes a two-piece frame that is placed around a patient. These pieces represent a lower "lumbar belt" and an upper "thoracic belt." The two belts are joined together by springs and/or coils and/or cushioned "pressure pistons." These elements exert a biasing force against the spine. The biasing force urges the top thoracic belt away from the lower lumbar belt, thereby relieving disc pressure. However, the connecting elements are generally rigid, limiting patient movement in flexion and extension.

U.S. Pat. No. 4,230,101, also entitled "Back Brace," offers a brace which seeks to control scoliosis by using vertical metal bars. The bars are positioned essentially parallel to where a healthy spine should be. U.S. Pat. No. RE31,564, entitled "Hyperextension Back Brace," also uses bars, with the bars positioned to apply resistance to restraining flexion. Again, somewhat rigid support mechanisms are presented.

Despite the number of back support devices available on the market and described in the patent literature, a need exists for an improved back support device. Particularly, there is a need for a back support device that more effectively exerts tensile forces on the upper torso of a user without causing tissue damage along the spine. A need further exists for a back support device that may be worn without the creation of contact sores and without significantly limiting range of motion. A need further exists for a back support device that offers a directed force on the torso to reduce compression on nerves, discs and degenerative tissue without restricting patient movement. This directed force is contextually responsive to the positions of the body to best protect and relieve the spine.

SUMMARY OF THE INVENTION

A back support device is provided herein. The device is configured to support a portion of a burden that would otherwise be borne by a user's spinal column and abdomen.

In one aspect, the device first comprises an upper support component. The upper component is dimensioned and arranged to be worn around at least part of the user's upper torso while residing under the user's arms. The upper component preferably comprises a network of fingers for effectively engaging the torso. More specifically, the fingers create a network of openings in the upper component that are dimensioned to engage the patient's ribs, thereby comfortably holding the upper torso in place without undue compression. In some instances, the network of fingers includes areas of increased thickness or increased stiffness for added stability or load bearing.

The device also includes a separate lower component. The lower component is dimensioned and arranged to be worn at least partially around the user's hips. The lower component may also cover at least a portion of the patient's lumbar spinal region.

The device further comprises a plurality of medial elements. The medial elements are supported by the lower component around the user's pelvic waistline. Each medial element is operatively connected to the upper and lower components so that each medial element may support a portion of the burden otherwise borne by the spine, thereby transferring the burden from the upper component to the lower component. Of significance, the medial elements are designed to be flexible, thereby permitting movement of the patient's upper torso.

Various medial elements are offered herein. These include the use of separate flexible rods placed around the user's torso. Alternatively, these include the use of so-called arcuate rails upon which coasters ride on opposing sides of the patient. Alternatively, these include the use of flexible tensioning bands woven around pulleys. The tension of the bands may be adjusted, either manually or through the use of programmed tensioning dials or through the use of selective anchoring of the bands along the lower support component.

BRIEF DESCRIPTION OF THE DRAWINGS

So that the manner in which the present inventions can be better understood, certain illustrations, charts and/or flow charts are appended hereto. It is to be noted, however, that the drawings illustrate only selected embodiments of the inventions and are therefore not to be considered limiting of scope, for the inventions may admit to other equally effective embodiments and applications.

FIG. 9A is an enlarged front view of the coaster of FIG. 8A, in one embodiment.

FIG. 9B is a right side view of the coaster of FIG. 9A.

FIG. 9C is an exploded right side view of the coaster of FIG. 9B.

FIG. 13A offers a front, or plan view, while FIG. 13B shows a side view. The ratcheting band control assembly is used to control the degree of load transferred from the upper support component to the lower support component.

DETAILED DESCRIPTION OF THE INVENTION

An improved back support device is provided herein, in various embodiments. In each embodiment, the device is configured to support a portion of a burden that would otherwise be borne by a user's spinal column and abdomen. The device is configured to be worn by a user under normal clothing. Preferred embodiments utilize a lower support component and a separate upper support component. This does not preclude, however, the use of an adequately flexible media for grouping the components into an easily donnable one-piece garment. Each of the lower and upper components radially encompasses a user, or patient.

Figure 1:
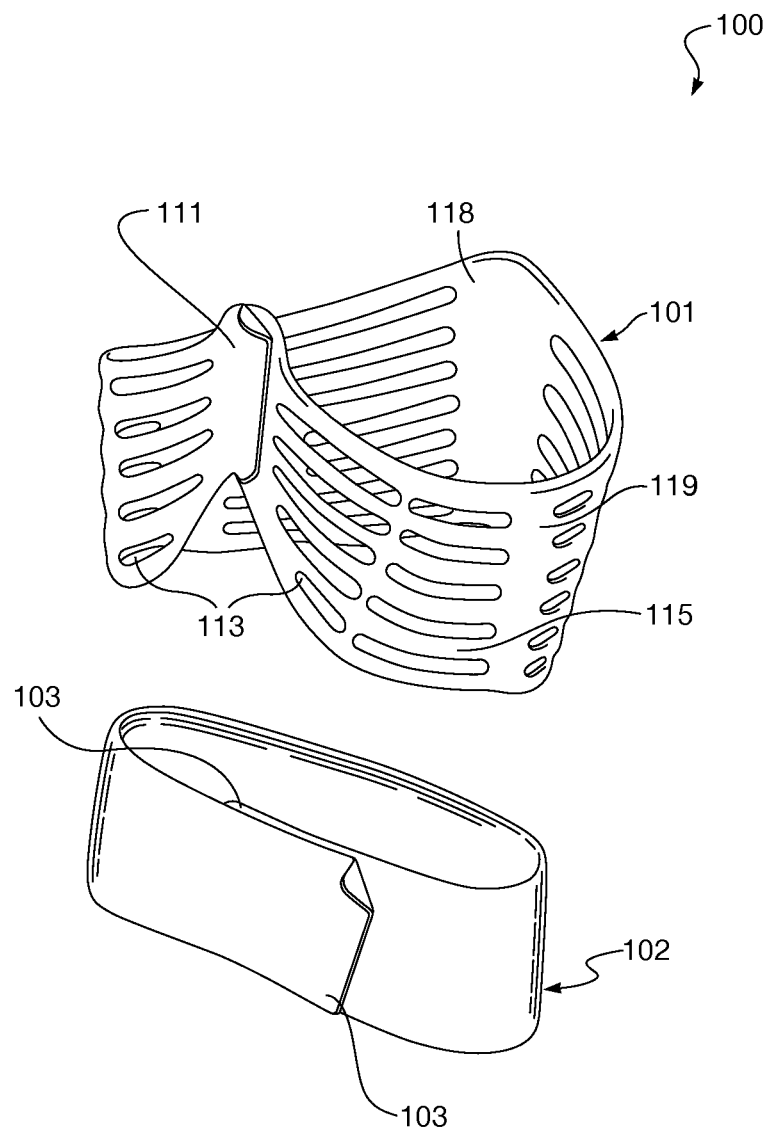
FIG. 1 is a perspective view of upper and lower support components as may be used in the back support devices of the present invention, in one embodiment. The upper component is configured to have a network of fingers for engaging the ribs and tissue of a user's upper torso.

FIG. 1 presents a perspective view of illustrative upper 101 and lower 102 support components. The components 101, 102 are indicated together in relative spatial relation at 100. The upper support component 101 may be referred to herein at times as a "glove," while the lower support component 102 may be referred to herein at times as a "belt." In some aspects, the components 100 form parts of the back support devices described herein in their various embodiments.

The components 100 are preferably fabricated from non-metallic and non-ceramic components, and should be dimensioned to fit comfortably under clothing. This permits the user to wear the components 100 and to pass through security detectors at airports, at government facilities, at corporate headquarters, and the like without activating alarms. In addition, the components 101, 102 should be fabricated from a material that has elasticity, or is compliant, and that can be adjusted to fit snugly around the user.

Referring now specifically to the upper support component 101, the upper component 101 has an anterior 111 (or front) portion and a posterior 118 (or back) portion. The anterior 111 and posterior 118 portions are dimensioned to wrap around the torso of a human user, generally covering areas just below and including the lower pectorals down to and just below the lower ribs. Ideally, the upper support portion 101 passes a comfortable distance below the user's armpits.

The upper support component 101 may be, in various embodiments, solid, graded, padded, or punctuated with cooling/adhesion holes. Preferably, the component 101 is separated into a network of fingers 115 defining holes 113 with solid separation areas 115. Thus, a "finger-like" form is provided. The solid separation areas 115 reside in an essentially horizontal direction to aid engagement effectiveness by gathering tissue and, in some areas e.g., ribs, aligning essentially with and exerting approximately vertical forces upon underlying skeletal elements when offloading is occurring. At the same time, the openings 113 accommodate tissue and aid in cooling or ventilation. Additionally, the openings 113 serve as voids to aid in flexibility and component weight reduction.

The benefit of the finger-like upper torso engagement structure may also be accomplished without the holes 113. For example, raised areas, preferably composed of a padding material, on the inside of the upper component 101 having an otherwise continuous surface (no holes 113) create a similarly shaped, aligned, and positioned array of effective fingers. These raised padded areas can be of varying heights and depths and shapes.

In yet another embodiment employing a finger-like body-engagement process, holes may be placed between raised fingers 115. In this arrangement, the holes 113 provide an additional (in addition to the raised-area fingers) structured tissue engagement component while also providing improved ventilation. For convenience herein, any of these or similar engagement structures are simply referred to as a network of fingers.

The upper support component 101 is preferably an integral device. The posterior portion 118 constitutes a continuous seam of material, while the anterior portion 111 releasably connects across the user's torso. Stated another way, a releasable connection may be provided at the user's sternum. This may include the use of hinges, buckles, snaps or a hook. Preferably, a hook-and-loop attachment is employed.

The support component 101 may have varying degrees of elasticity. Further, the component 101 may include areas of additional thickness or areas of increased stiffness to provide extra support or rigidity to select areas. This means that the network of fingers 115 may contain areas of different thickness or areas of different tensile strength, or combinations thereof.

It is observed that in the embodiment of FIG. 1, a biomimetically adjusted arrangement is used for the fingers 113. Rather than being perfectly horizontal, the fingers are both angled and curved to approximate the location and curvature of the underlying ribs of the user. This option provides additionally aligned interface contact at every level and, when the glove 101 extends just below the ribs as tracked around the torso, this further enables a comfortable amount of mechanical lift which will result in improved engagement for the offload of spinal burden.

The upper support component 101 may be fabricated from any of a variety of materials, including those commonly used in compliant braces. However the comfort of the user may be affected by a material or form factor that is too hard, too soft, non-porous, poorly aerated or too weak under loading conditions to support the load. Preferred materials for the glove 101 are semi-rigid to rigid with a fiber base that permits reasonable load bearing with very thin components. This allows enough flexibility for the user to breathe effortlessly and enough rigidity, at least at points of heavy load concentration, to transfer loads without buckling. Very thin multiple layers of fiberglass may be used to provide sufficient rigidity to the structure. A preferred fiber is carbon used with a resin-based binder to permit thin components to fit well under clothing.

Figure 2:
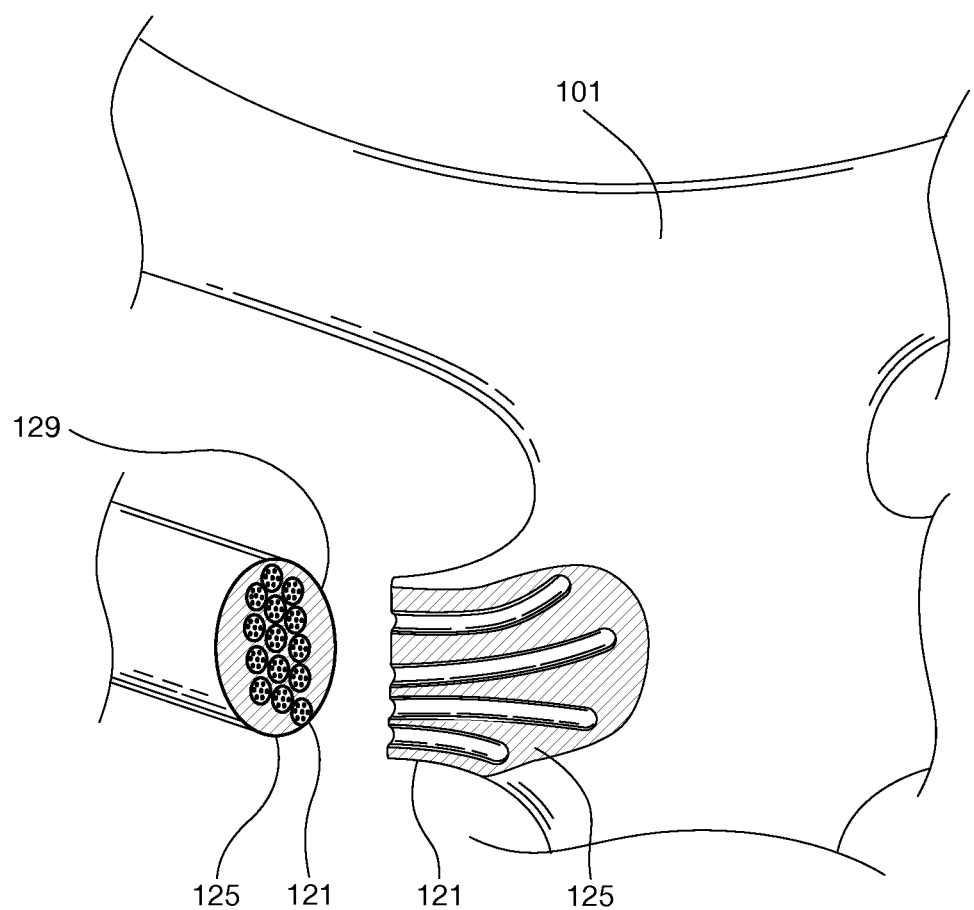
FIG. 2 is a cut-away view of a portion of the upper component of FIG. 1, in one embodiment. A part of the component structure is exposed.

One example of a suitable material is a Shore-A 80 polyurethane rubber. FIG. 2 is a cut-away view of a portion of the upper component 101 of the back support device 100. A part of the component structure is exposed. Polyurethane rubber is placed in and over multiple layers of carbon fiber 121 cut or formed in the shape of the upper orthotic device 101 and laid up to cure in the form of the wearer. This may involve the formation of a mold, or "positive," of the desired human form and dimensions. FIG. 2 shows a partial view of the left side portion (119 in FIG. 1) of the glove 101 with a section of material removed showing a rubber binder 125 and imbedded carbon fibers 121. However, any material with adequate support and comfort is appropriate for the upper support component 101.

An inner fabric layer (between the glove and the user's skin) or a sprayed-on fabric composite on the inside of the glove 101 may be used to provide a skin-friendly and sweat-absorptive layer. Various stretchable materials have been developed for sports and space that provide good skin interfaces. Many of these materials absorb sweat; some enhance circulation while refusing to clump into moist, irritable creases associated with binding sites and friction areas. However, those that severely reduce friction can be problematic. In this respect, such materials may require, for example, that the inside surface better adhere to it, e.g., with a rough surface or other adhesion augmentation. Examples include the male portion of a hook-and-loop surface, Van Der Waals enhancing fibers, etc. While the space and sports materials are applicable to the support component 101, an ordinary cotton composite or fabric can actually be preferable to the slippery surfaces associated with some sweat-control fabrics. Thus, though not required, the skin interface may be applied directly to bare skin, especially in embodiments where an inner protective layer is provided on the upper support component 101.

Referring next to the lower support component 102, or belt, the lower support component 102 is preferably fabricated from a continuous pliable material, and is dimensioned to wrap around the hips of the user. Ends 103 of the belt 102 are joined using clips, snaps, hinges, buckles or, more preferably, a hook-and-loop attachment. In one aspect, the lower component 102 covers a lower portion of the user's lumbar region in a compliant and snug manner.

The belt 102 will typically be worn on the user's pelvic waistline, referred to herein as the "hips," defined by an area surrounding the hips from an upper rim at the lower waist and continuing down approximately 4 to 7 inches depending on the stature and adipose magnitude of the wearer. In the preferred embodiment, the belt 102, though essentially rigid at load-bearing points, has some flexibility and the brevity of its length and its body-shaped curvature minimizes interference with normal body activity. Like the upper support component 101 described above, the belt 102 may be made of any material. However, in the preferred embodiment, the material is built up to have extra strength (e.g., additional thickness or stiffness) at points with concentrated loads. Fiber patterns are preferably arranged to provide the most support in desired support directions. In a preferred embodiment, the material at the posterior (rearward) sagittal (central plane dividing body's right from left) intercept is flexible in that narrow strip in the direction that allows it to emulate a vertical hinge thus allowing the otherwise supportive posterior of the belt 102 to bend in the chosen dimension. The gradient of flexibility from sagittal softness towards load bearing rigidity at points of heavy medial element support makes the belt 102 more flexible while providing full vertical support to medial elements (described in greater detail below).

It is observed that one of the functions of the belt 102, in certain embodiments, is to secure medial elements that extend between the lower support component 102 up to the upper support component 101. In this way, the belt 102 receives a transfer of load from the upper support component 101. By discretizing load density at key points, the belt 102 can remain generally thin and lightweight while carrying out its load-bearing function.

Figure 3A:
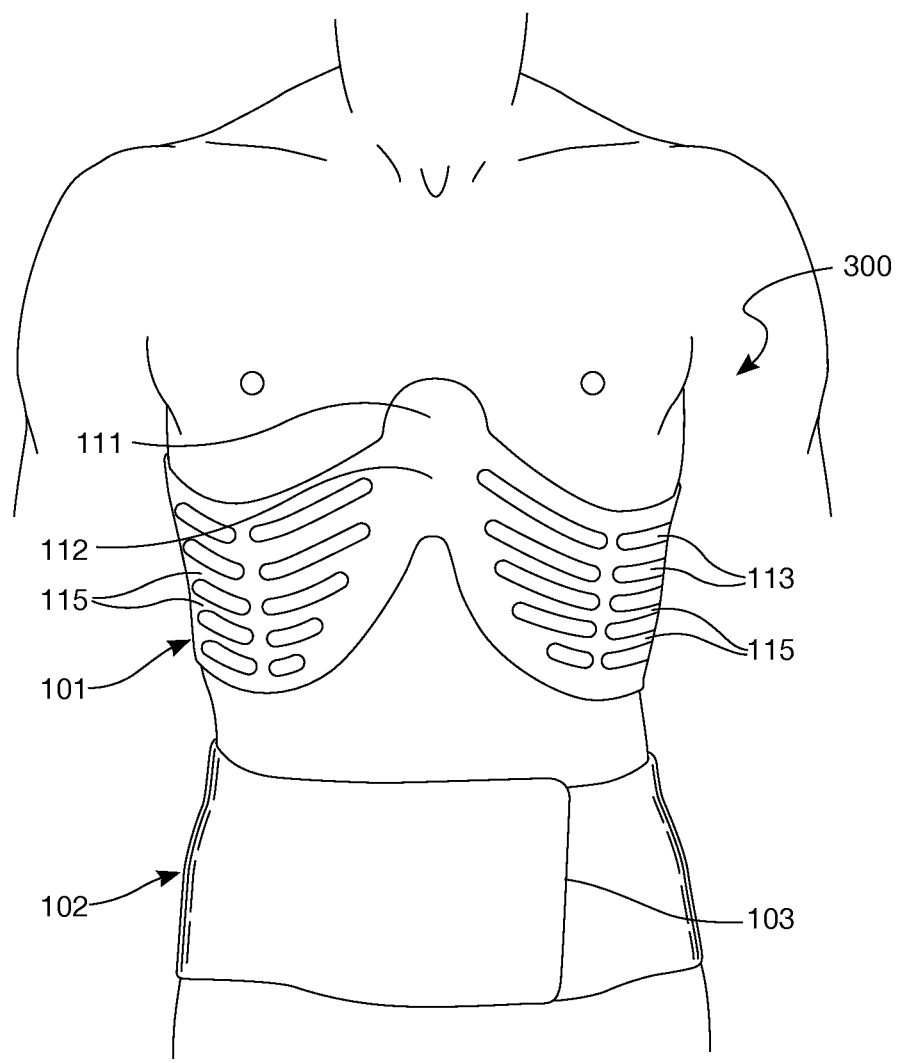
FIG. 3A is a front view of the upper and lower support components of FIG. 1, presented on the torso of a user. In this arrangement, no medial elements are shown.
Figure 3B:
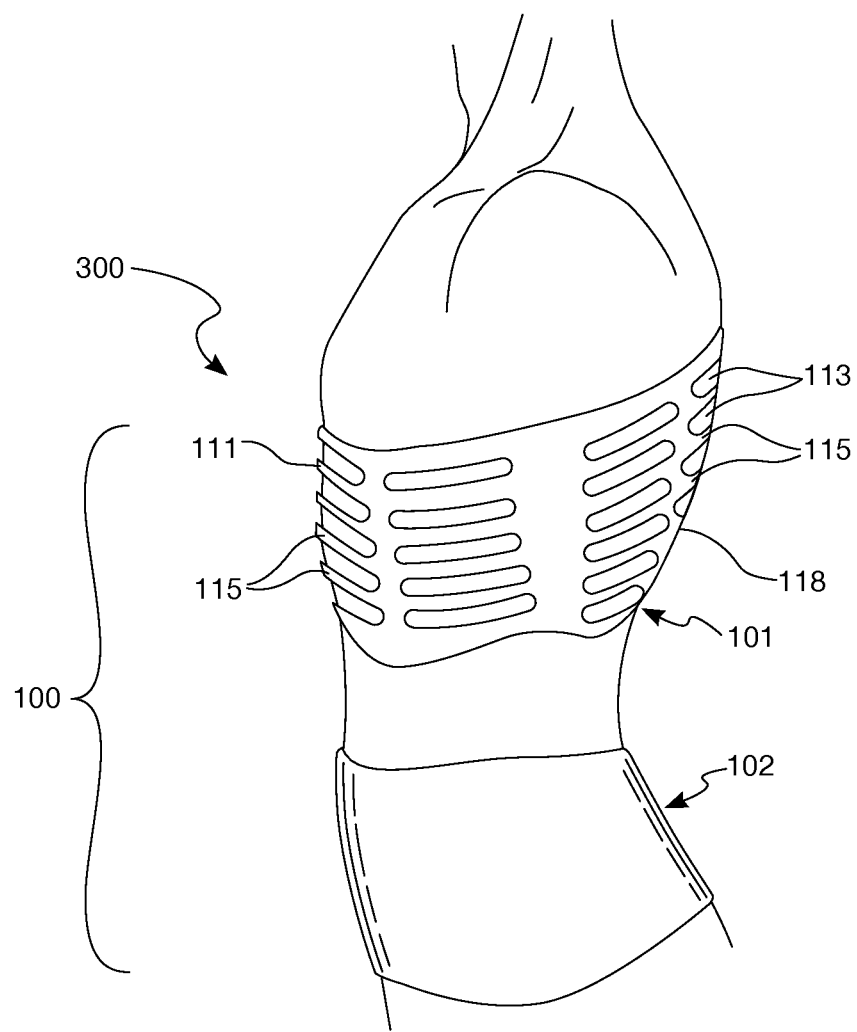
FIG. 3B is a side view of the upper and lower components of FIG. 1, again presented on the torso of a user.
Figure 3C:
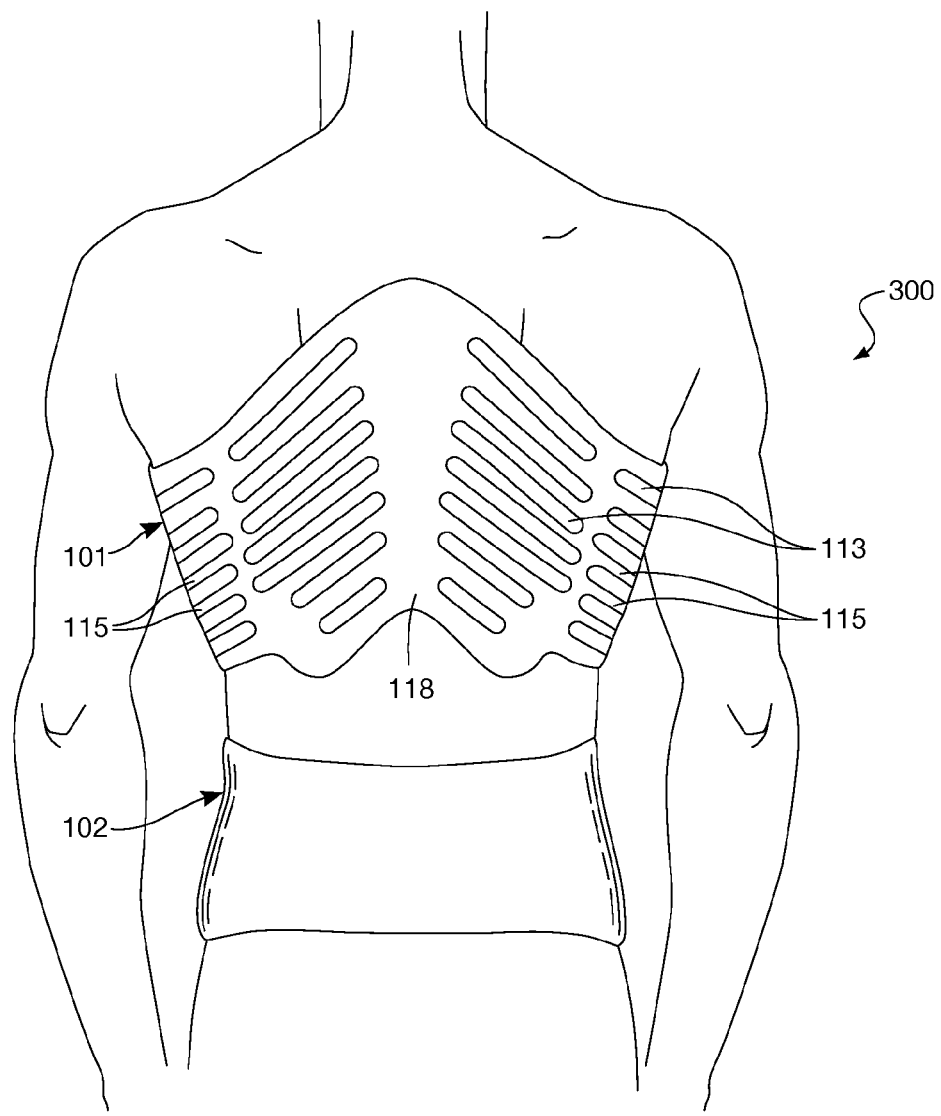
FIG. 3C is a rear view of the upper and lower components of FIG. 1, again presented on the torso of a user.

FIGS. 3A, 3B and 3C provide additional views of the back support components 100. FIG. 3A is a front view of the components 100 of FIG. 1, presented on a torso 300 of a user. An edge 103 of a hook-and-loop flap of the belt 102 is seen. Here, the edge 103 lays down over the similarly shaped sternum flap from the left side of the belt 102.

FIG. 3B provides a side view of the components 100, while FIG. 3C shows a posterior view. In these views, the open spaces 113 of a the network of fingers 115 are more clearly visible. No medial elements are shown in these views.

The upper 101 and lower 102 components may be made of a uniform material. Additionally, the components 100 may use hinges, ratchet tighteners, buckles, or other connecting devices to connect components or panels. In one preferred embodiment, the material is constructed to be orthotropic, and varies in thickness based on amount of anticipated load at particular points. By arranging orientation and number of layers of the fiber substrate, such as by selectively arranging fiber weave patterns and thicknesses to achieve dimensional support bias, a vertically supportive area can be flexed in a horizontal direction. For example, the upper support component 101 may be constructed to bend to facilitate closing and opening for donning and doffing, respectively. Thus, when it is not desirable to have a vertical hinge to facilitate this opening, the material can be biased to bend more easily in this dimension (laterally as if on a vertical hinge), thus providing vertical support in a material that more easily bends in a non-supportive dimension.

To minimize bulk and weight, the glove 101 is preferably stronger at points of stress such as by providing additional layers of fiber and stronger binding compounds and increasing gradually up to points of stress from points of less stress. Where load level permits, this can be alternatively or additively accomplished with a narrow, typically vertical, band of more flexible material where the partial bend should occur.

In FIG. 3C, an embodiment where the bendable or otherwise flexible (effectively hinged) posterior area 118 is in the central area of the back over the spine is illustrated. In this embodiment, as the two sides of the glove 101 close around the user's torso 300, bending at the orthotropically favored area in the back, the two sternum covers (shown at 112 in FIG. 3A) have complimentary hook-and-loop layers, making a snug adjustable fit. By allowing more overlap than is shown (e.g., wider sternum covers), more adjustability is added.

Figure 4A:
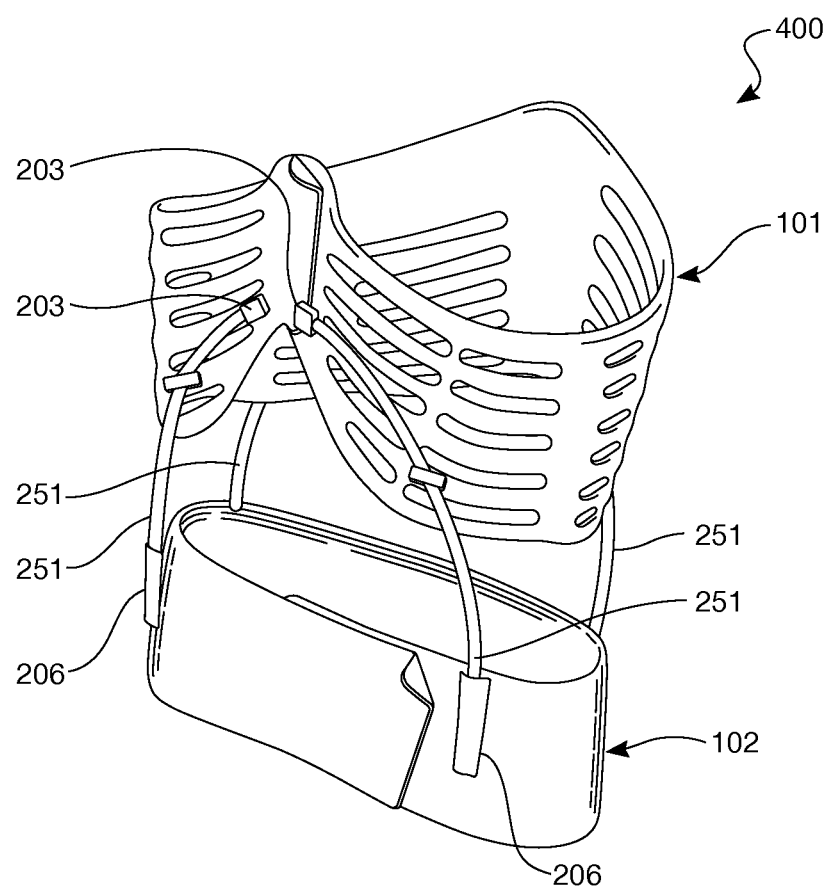
FIG. 4A is a front perspective view of a back support device of the present invention, in one embodiment. The upper and lower support components of FIG. 1 are shown. Here, medial elements in the form of flexible rods that connect the upper and lower support components are provided.

As indicated above, the spatial separation of the upper 101 and lower 102 components are mediated by one or more intermediate supportive components. These are generally referred to herein as "medial elements". Medial elements are not shown in the view of FIG. 1 or in the FIG. 3 series of drawings. However, FIG. 4A shows a front perspective view of a back support device 400 of the present invention, in a first embodiment. Here, medial elements 251 are shown connecting the upper 101 and lower 102 support components.

In the arrangement of FIG. 4A, four separate medial elements 251 are shown. Applicable medial elements 251 include any parts connected to the glove 101 and belt 102 that offload weight supported by the glove 101 to the belt 102. Thus, any flexible or resilient material can be used that meets this purpose. In the preferred embodiment, intermediate elements 251 define flexible rods that allow the torso of the user to bend while still transferring force from the glove 101 down to the belt 102. The rods 251 provide a separating action between the upper 101 and lower 102 components to actively reduce spinal load without restricting user movement or unduly compressing the torso.

Figure 4B:
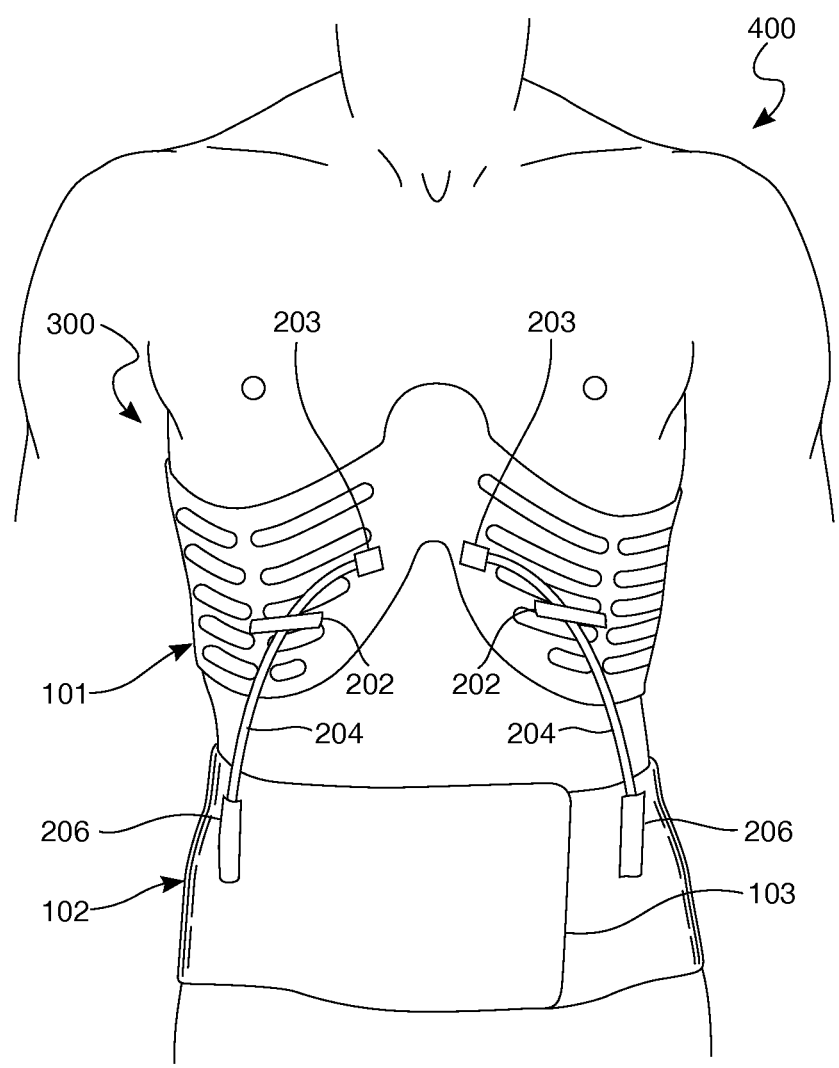
FIG. 4B is a front view of the back support device of FIG. 4A, presented on the torso of a user. Body guides are seen providing limits for movement of the front medial elements.
Figure 4C:
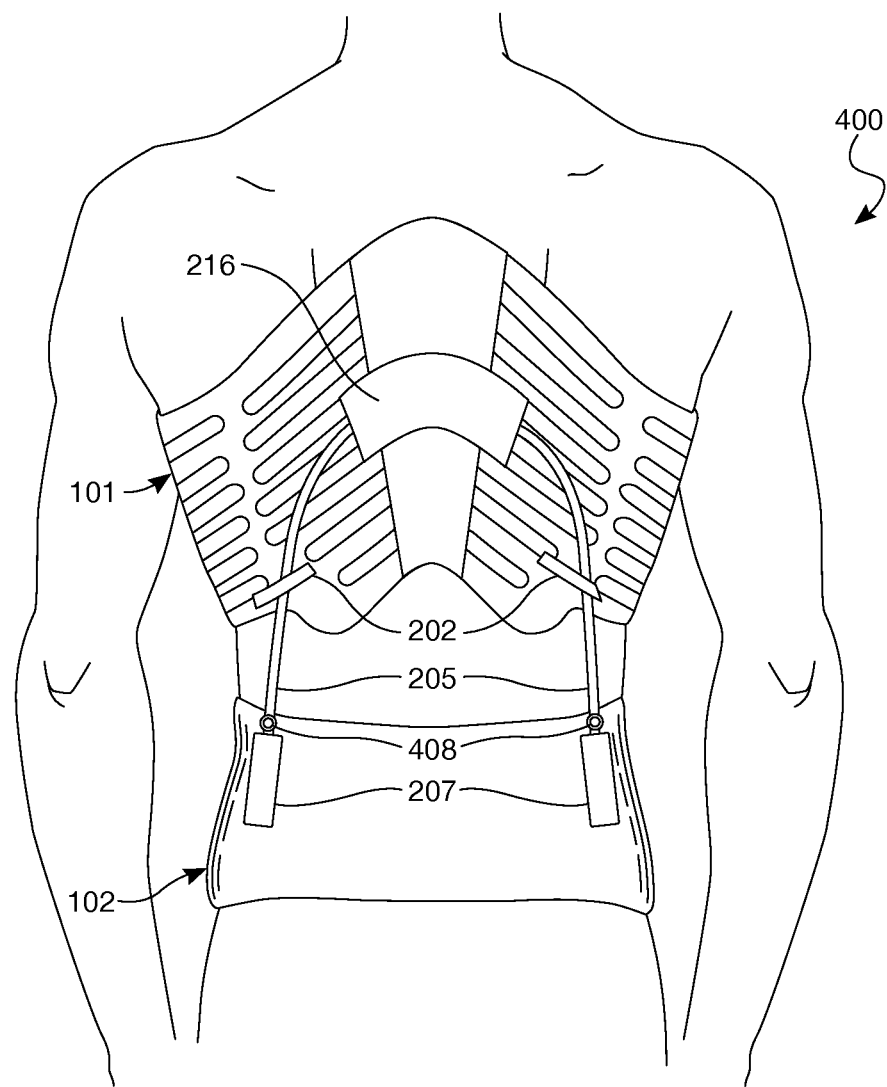
FIG. 4C is a rear view of the back support device of FIG. 4A, again presented on the torso of a user.

In the arrangement of FIGS. 4A, 4B and 4C, pairs of medial support elements 251 are employed. Specifically, each side of the device 400 presents two separate medial elements 251, with each element 251 connecting the upper 101 and lower 102 support components. Each pair of elements 251 includes an anterior element and a posterior element. Anterior elements (numbered 204) are shown in FIG. 4B, while posterior elements (numbered 205) are shown in FIG. 4C. Each element 251 is attached to the glove 101 at 203, and is attached to the belt 102. For the anterior elements, attachment is at 206; For the posterior elements, attachment is at 207. Attachment points 206 and 207 preferably include flaps or panels that cover the connections, both for aesthetic purposes and to prevent hang-ups on clothing.

FIG. 4B shows a front view of the back support device 400 of FIG. 4A, while FIG. 4C is a rear view of the back support device 400. In the views of FIGS. 4B and 4C, the device 400 is presented on a torso 300 of a user. Body guides 202 are provided for the medial elements 251 intermediate the connection points at 203 and 206. The body guides 202 limit movement of the elements 251 relative to the upper support component 101.

In the device 400 of the FIG. 4 series of drawings, the elements 251 are in the form of flexible and resilient rods. During use, and when the medial elements 251 are deflected (e.g., compressed) responsive to an essentially downward force from the torso 300, a portion of the burden that would have otherwise reached the spine is offloaded to the belt 102. Force is then transferred through the belt 102 and to the user's hips.

Along with the medial elements 251, it is desirable to be able to adjust the tensioning energy stored in the medial elements 251. In this way, more or less force may be offloaded to the belt 102.

In one aspect, the medial elements 251 may be manually tensioned by placing the lower portion in special holsters. Such holsters are shown at 206 in FIG. 4B (for the anterior side) and at 207 in FIG. 4C (for the posterior side). Holster 201 receives anterior elements 204 (FIG. 4B), while holster 207 receives posterior elements 205 (FIG. 4C). In addition, the position of the medial elements 204 and 205 may be adjusted by adjusting the guides 202.

Figure 4D:
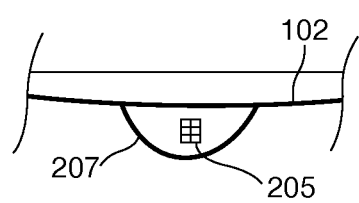
FIG. 4D is a top view of a holster as may be used in the lower support component, or belt, of the back support device of FIG. 4C. A section view of a rail is seen.
Figure 4E:
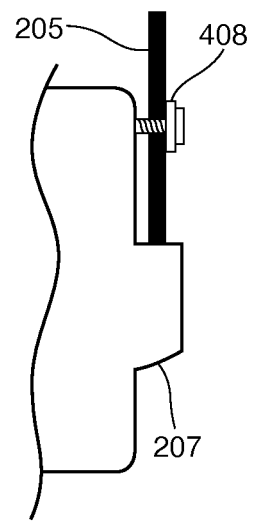
FIG. 4E is a side view illustrating one embodiment of the holster as may be used in the back support device of FIG. 4C.

FIG. 4D is a top view of the posterior holster 207 as used in the lower support component 102, or belt, of the back support device 400 of FIG. 4A. A section view of an element 205 is seen. FIG. 4E is a side view illustrating one embodiment of the posterior holster 207. Of interest, a fastener 408 is shown. The fastener 408 is optionally used to bind the medial element, or rail 205, from axial (essentially up and down slipping) and lateral travel by tightening a screw that draws the fastener 408 to bind the medial element 205 against the belt 102.

In one aspect, the holster 207 is constructed from a compliant material that is, in turn, supported by a rigid material. The holster 201 comprises an outer shell comprised of a rigid material, and an inner portion, surrounded by the outer shell, comprised of the resilient compliant material. A rod end is positioned within and extends from the inner portion, thereby allowing at least slight bending of the portion of the rod end embedded within the inner portion.

It is also observed that, in lieu of using two separate medial elements 204, or two separate medial elements 205, on each side of the device 400, a single medial element may be used on each of the anterior and the posterior sides. In this instance, in lieu of connecting the separate medial elements 204 or 205 to attachment points 203 on the upper support component 101, the medial elements 204, 205 will comprise continuous elements that arch across the component 101. Stated another way, the medial element 251 is a continuous arching rod, or rail, terminating at both ends in holsters 207. In this instance, the attachment points 203 will be pouches or sleeves 216 that slidably receive the respective elements 204, 205. This embodiment is demonstrated in the FIG. 8 series of drawings, discussed below.

The progress of the deformation of rods 204 and rail 205 may also be controlled and/or limited to safe ranges of user movement by physical range limiters to prevent the spine from injury (or re-injury) when traveling too far or when being compressed too much axially. In the devices 400 of the FIG. 4 series, this is done through the use of the body guides 202. Thus, the overall flexibility of the back support device 400 may be tuned by adjusting the vertical and lateral location of the body guides 202, here shown attached to the glove 101. Additionally, flexibility of the body guides 202 to deformation may be used to control the effective mobility range. Flexing at the waist, for example, will cause the rods' 204 curvature to change. The amount of resulting travel is limited by the body guides 202, thus reducing the ability of the rods 204 to comply, making it react with more stiffness. More body guides 202 than shown can be used to apply different ranges of motion to different parts of the rods 204. The distance away from the center of the body, both through the shape and the flexibility of the body guides 202, can also be used to control the distance of medial element 204, 205 travel.

It is also noted that the stiffness and length of the medial elements 204, 205 as well as the user's height will be contributing factors to the level of support. Normally, within the performance limits of the material and structure of the medial elements 204, 205, increased medial element deflection responsive to an increase in instant torso burden will result an increase in force exerted by the medial elements 204, 205 and, correspondingly, an increased offload magnitude.

The use of medial elements 204, 205 allows vertical forces to be exerted on the upper support component 101. Further, such forces exceed the essentially downward force of the torso 300 on the upper support component 101. This is referred to as spinal distraction. Thus, when the offloaded forces responsive to the stored energy in the medial elements 204, 205 exceed the instant torso burden to the spine, a distracting force to the spine is beneficially created.

Controlled distraction is considered advantageous for certain spinal conditions. It is also believed that the ability to provide a selected magnitude of distraction over a potentially long enough period of time for change to occur with even gentle distraction can be safer and more effective than rapid, short-term distraction therapy. Thus, it is desirable to not only provide a back support device offering so-called distraction (such as in FIG. 4A), but to also be able to "tune" the device. For example, if it is desired to bias a back support device towards right lateral flexion, then the rods 251 on the left side of the device 400 of FIG. 4A may be made to be slightly longer, or slightly stiffer, than the rods 251 on the right side of the device 400. Similarly, if it is desirable to improve the upward posture of a patient, then the posterior rods 204 of FIG. 4B may be made slightly stiffer, or slightly longer, than the anterior rod 205 of FIG. 4C.

Figure 5:
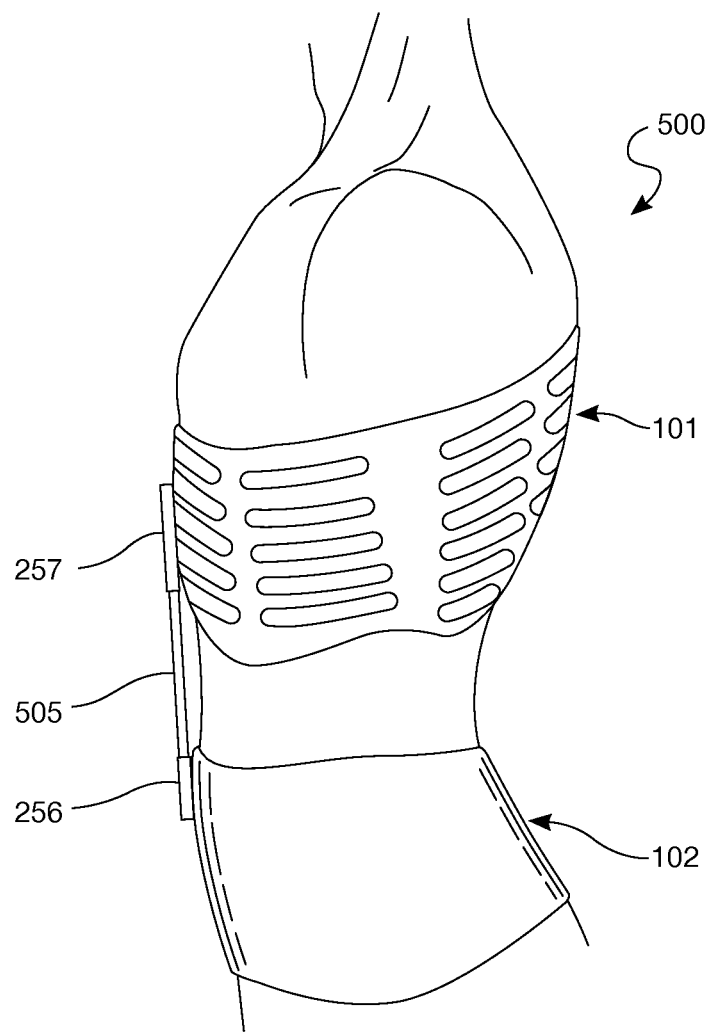
FIG. 5 is a side view of a back support device of the present invention, in an alternate embodiment. The upper and lower support components of FIG. 1 are again employed. Here, an anterior medial element has been placed in the sagittal plane, connecting the upper and lower support components.

Another way of biasing a back support device is presented in FIG. 5. FIG. 5 is a side view of a back support device, noted at 500. Here, the back support device 500 includes a single anterior medial element 505. The medial element 505 has been placed in the sagittal plane, connecting the upper 101 and the lower 102 support components. The medial element 505 may again be considered to be a rod.

In the arrangement of FIG. 5, the medial element 505 is considered to be a passive element. The passive element 505 may be a cylindrical rod, a rectangular rod, or a bundle of flexible rods. When the term "rod" is used herein, it is understood that such is not limited to a particular profile or stiffness. Opposing ends of the medial element 505 of FIG. 5 reside in holsters. Holster 256 resides on the lower support component 102, and receives and supports a lower end of the rod 57505. Upper holster 207 resides along the upper support component 101 and receives an upper end of the medial element 505.

Figure 6A:
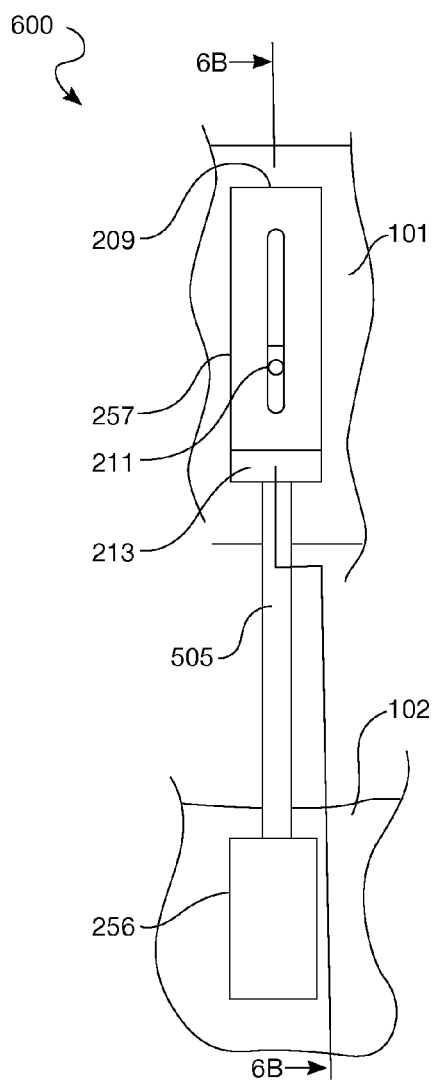
FIG. 6A is a front view of the anterior medial element of FIG. 5, in an assembly.

FIG. 6A is a front view of the anterior medial element 505 of FIG. 5, in a rod control assembly 600. Visible in FIG. 6A are the motion-limiting holsters 256, 257 and the rod 505. The rod 505 is designed to connect the glove 101 and the belt 102. When the user bends forward, the passive element 505, while bending with the body, slides further into the holster 257, optionally guided by tracking pin 211, until the rod 505 reaches the closed end 209 of the holster 257 at the top whereupon flexion is most firmly resisted or stopped altogether depending on the stoutness and stiffness of the passive element. A bottom end 213 of the holster 257 may include a compliant material to keep the radius of curvature of the rod 505 from causing breakage.

Figure 6B:
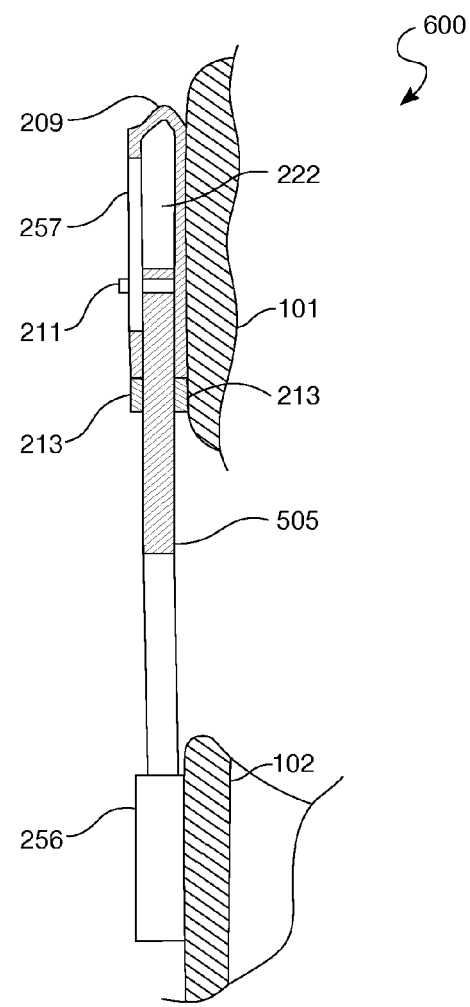
FIG. 6B is a sectional view from the left side of the medial element shown in FIG. 6A, with the section following the line 6B-6B in FIG. 6A.

FIG. 6B shows a partial cutaway side view of the anterior portion of the assembly 600. It can be seen here that holster 257 includes a through-opening at the bottom to receive the upper end of the rod 505 When the user is vertical, an empty space 222 opens up above the rod 505. In an optional embodiment not illustrated in FIG. 6B, the space 222 may be filled with a flexible foam or rubber, or house an essentially vertical spring, between the top and bottom of the space 222 to at least partially resist the movement of the rod 505 as it enters space 222. Ideally, the space 222 will receive the rod 505 during flexion.

Modifications may be made to the holsters 256, 257. In one aspect, the entry points to a holster, such as 206 in FIG. 4B, can include a compliant or rubberized material. The compliant material helps keep the radius of curvature of the medial element from causing breakage. Alternatively, the holsters 256, 257 can include a pin that permits at least some tolerance to allow rotation of the medial element, or rod 505.

Passive element assemblies, like rod control assembly 600, may be placed wherever a path is desired to be limited. The assembly 600 may be used in pairs equidistant from the sagittal plane (for flexion control) or from the coronal plane with a pair on each side (for lateral bending limits) to provide balanced control. Such an assembly 600 protects the user from moving beyond a safe action range. The assembly 600 may also be used in coordination with other range-protective elements.

Figure 7A:
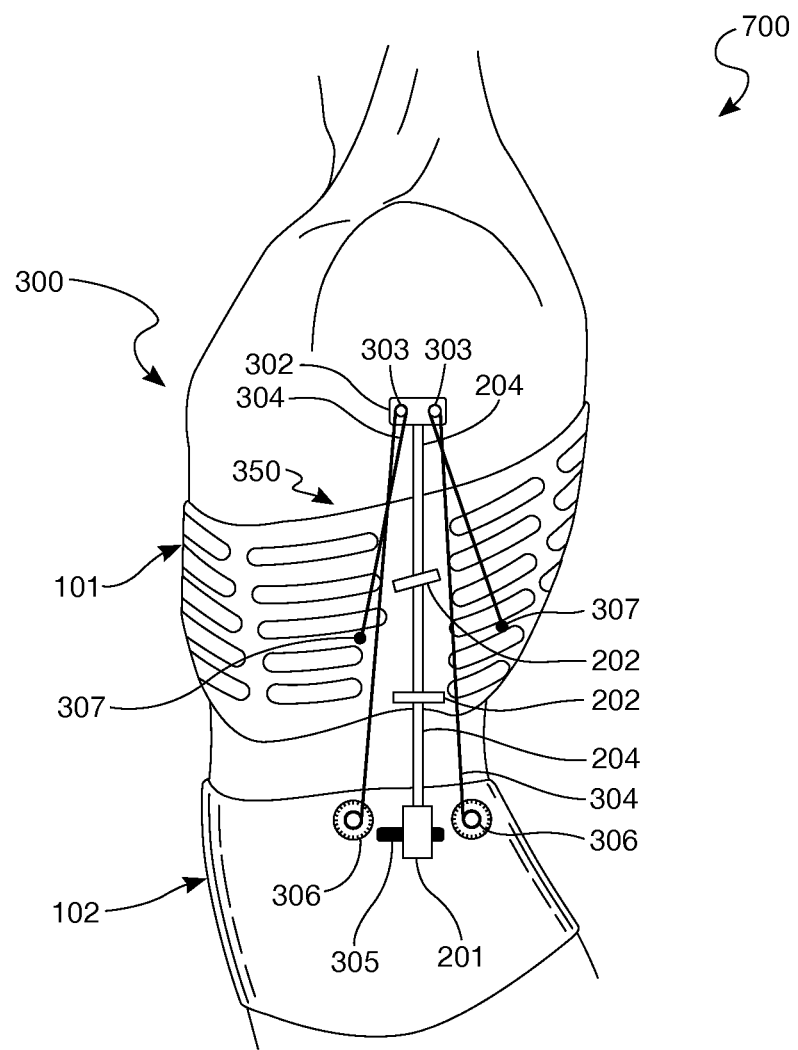
FIG. 7A is a left side view of a back support device of the present invention, in alternate embodiment. In this view, a single flexible rod is shown connecting the upper and lower support components on a side of a user. Further, support tensioning bands are employed as part of the medial elements.
Figure 7B:
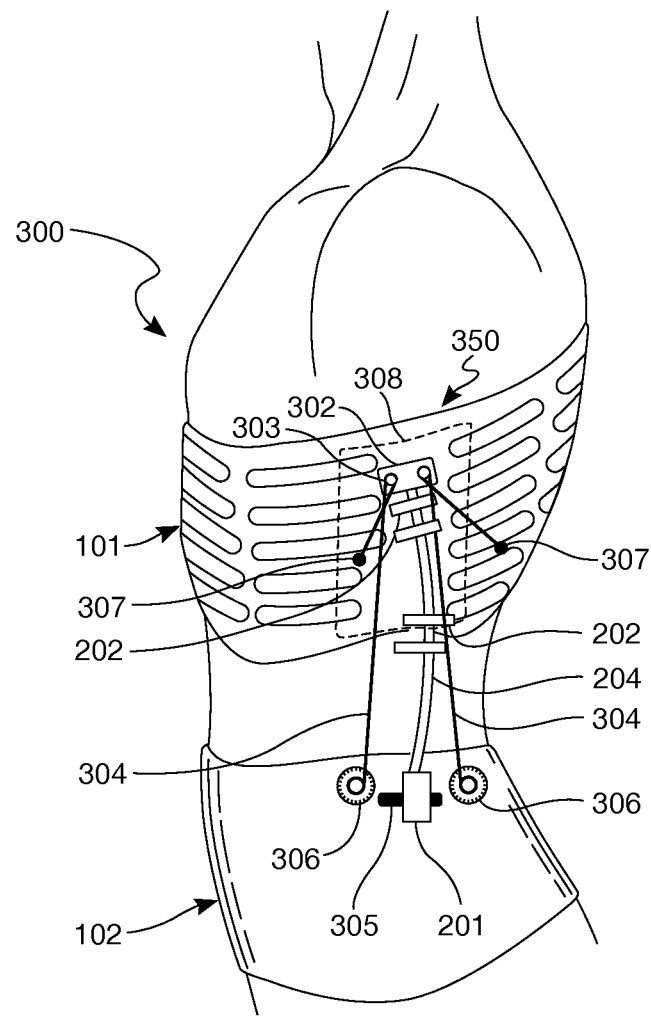
FIG. 7B is another side view of the back support device of FIG. 7A. Here, the flexible rod is deflected under load responsive to a tightening of the tensioning bands.

FIGS. 7A and 7B present an embodiment for a back support device 700 which provides the ability to adjust the intermediate element's load sharing characteristics. This is done through the use of tensioning bands 304.

FIG. 7A is a side view of a back support device, in alternate embodiment, indicated at 700. In this view, an elongated medial element 204 is shown connecting the upper 101 and the lower 102 support components. The medial element 204 is in the form of a vertical rod. Lateral movement of the vertical rod 204 is controlled or limited by the selective placement of body guides 202 along the upper support component 101.

The flexible rod 204 works in cooperation with support tensioning bands 304. The tensioning bands 304 are lightly tightened to apply a degree of tension to the rod 204. A combination of the rod 204 and tensioning bands 304 is provided on each of the left and right sides of the back support device 700.

In the arrangement of FIG. 7A, the medial element 204 is in an unloaded position. The user is in a generally upright position. In addition, the tensioning bands 304 are relatively loose. The bands 304 may optionally be tightened to provide additional distraction force.

FIG. 7B is another side view of the back support device 700 of FIG. 7A. Here, the medial element 204 is deflected under load responsive to a tightening of the tensioning bands 304. The supporting element 204 is under compression. Of interest, the element, or rod 204, is sharing the burden normally carried only by the user's back and midsection. The glove 101 is higher in FIG. 7B than in FIG. 7A.

In the arrangement of FIGS. 7A and 7B, medial elements 204 are in the form of rods. The rods may be made of graphite, fiberglass, spring components or any material that flexibly deforms under load, exerts a resistive force and, in the preferred embodiment, returns essentially to the original shape when the load is removed. While these passive elements will probably most often be used in coordination with other components to relieve, at least in some part, axial (downward) pressure on the spine, these elements also have application for independently aiding trunk extension (e.g., an element or elements in front as in the medial elements 204 in FIG. 4B) or aiding or biasing load supportive of lateral bending (e.g., an element on one side of a wearer to offset an undesired lateral lean caused by injury, atrophy, scoliosis, neuro-control problems (like stoop posture in Parkinson's) or other deforming factors).

In the arrangement of FIGS. 7A and 7B, the rod 204 defines a straight-at-rest embodiment. Other essentially straight-at-rest options include leveraged embodiments. Leveraged embodiments provide advantages in "throw distance," that is, the distance the upper support component 101 can move up and down in response to changes in load without loss of support, ease of handling, and ease of donning and doffing. The rod, i.e., any intermediate element 204 which may come in a variety of embodiments besides a simple rod, represents a preferably flexible support (or a bundled or unbundled batch of rods or other shaped poles) which, at rest in this illustrated embodiment, can be essentially straight at this stage but is preferably pre-curved slightly and is anchored caudally by the holster 201.

It can also be seen in FIGS. 7A and 7B that a holster 201 is used to secure the medial element 204 at a lower end. However, there are any number of securing supports applicable to the current invention. For example, the holster can be fixed rigidly to the belt 102, or less constrained e.g., connected to the belt 102 such as with connector 305. Friction control and/or click control and/or torsion spring control can be used to manage medial element dynamics.

To remove undue stress where the medial element 204 enters the holster 201, hybrid embodiments will include connectors 305 where the holster 201 offers a rotational tolerance/limit path for the rod 204. This increases the radius of curvature as the medial element 204 (or 205) enters the holster 201. These optional holster elements are useful for permitting desired degrees of freedom allowed by the connection and/or changing the mechanics of the joint. For example, a pinned joint permits rotation but can mediate rotational force resistance, while a fixed connection allows no rotation but can transmit bending moment.

Similarly, for posterior medial support in FIG. 4C, a continuous arcuate rail 205 under an optional covering 216 provides lift that, in this illustrative embodiment, is applied to posterior load transference to the belt 102. Of interest, the various components described above can be used individually or in combination. For example, the single anterior lifting support provided by medial element 205 of FIG. 5 can be used alone to improve the posture of a forward flexing wearer, or, it can be combined with the posterior support elements 204 of FIG. 4B to provide essentially balanced lift. That is, both front and back are lifted so that, rather than biasing the flexion or extension of the body, they together provide a net lift that offloads weight from the glove 101 to the belt 102, bypassing load to the back.

In the preferred embodiment, all medial elements tend to conform to the body shape comfortably and closely. They are easily guided by loops and brackets (such as body guides 202) attached to the upper 101 support component, and are tolerant of extremes in minimum radius of curvature without loss of full recoil return and with consistent force exertion in the desired dimension. The medial elements also preferably track body motions well and have a power to bulk ratio favorable for wearing invisibly under clothing with a flexibility conducive to hugging the body comfortably during motion. Embodiments of the back support devices herein offer elastic and also powered options for mediating a controlled degree of enforced separation between the upper 101 and lower 102 support components as long, that is, as they transfer a portion of the upper body load from glove 101 to belt 102. The amount of force offloaded by the back supporting device 400 will preferably be tuned to be responsive to:

a. Instant wearer condition (more support may be needed towards the end of a long work day, at the first sign of renewed pain, or responsive to a pre-emptive sensor-captured indication of a problem);

b. The amount of assistance needed responsive to the weakness, body weight, amount of pain, loss of muscle function, and physical performance ability of the user;

c. The task at hand (more support is required for heavy loads or extended periods of labor);

d. The current degree of wearer recovery (less support responsive to a more nearly healed condition at the end of a regimen thus allowing enough burden to encourage an increase bone density); and e. Slippage in glove and/or belt. Here the adjustment corrects the slippage in addition to ordinary adjustments for support.

It is also observed that the rods 204, 205 may be selected based upon their stiffness or slenderness ratio (expressed as the ratio of diameter to length) to be effectively unyielding. In this instance, the responsive adjustments to user instant change are accommodated by any one or combination of the follow factors:

a) A first factor is the tolerance for shifting provided by a body guide 202. In this respect, the body guide 202 may be arranged to stretch up to a point. While body guides (medial element path limiters attached to the body of the glove) will often be rigid elements having through-holes that allow the rod to move only within the area provided by the through-holes, the body guide 202 may also be in the form of a flexible band. Thus, the rod 204 or 205, confined between the flexible band and the surface of the glove 101 may travel between the attachment points (where the body guide 202 is attached to the glove 101), and additionally, to the extent that the band's flexibility permits, some additional travel is allowed.

b) A second factor is the slight shifting of flesh under the upper 101 and lower 102 support elements.

c) A third (and optional factor) is the use of automatically adjusted tensioning means. Such an adjustment mechanism is shown at 306 in FIG. 7A, discussed below. The tensioning means 306 may employ powered and automatically adjusted dials, e.g., responsive to sensors.

d) A fourth factor is the presence vel non of a compressive media or spring in space 222 residing in an upper holster 207 of FIG. 6. The media serves as a biasing force that resists further entry of the rod 505 into the space 222.

e) A fifth factor is the stiffness of the medial element, such as a rod 204. Flexible rods are preferred, as rods that can bend and then recover store beneficial energy. It is helpful for this embodiment to start the rod off with at least a slight curve to effect a bias for a preferred plane to bend within so that the rod behaves the same way from an at-rest state each time. While this is not necessary, it is advantageous. The flexible rods can reduce shock from user motion. When the user bends forward (flexion), the rods bend as well (compare FIGS. 7A and 7B for change in rod 204 shape). A variety of materials may be used for the rods 204, 205, including fiberglass and carbon fiber rods. These materials work well and with an impressive load range despite minimal weight.

In various embodiments described herein, the rod 204, 205 is relatively free to move vertically and laterally within the confines of the body guides 202 and holsters 201. In one aspect, such as the one shown in FIG. 7A, an upper end of the rod 204 is secured to the upper support component 101 only by means of the body guides 202. An upper end of the rod 204 is connected to a T-plate 302. The T-plate 302, in turn, houses a plurality of pulleys. Illustrative pulleys are shown at 303. The pulleys 303 are part of a cable control assembly 350 that includes a tensioning band 304. The pulleys 303 act as wheels that receive tensioning bands 304 on opposing sides of the rod 204. Preferably, the pulleys 303 have lubricated bearings that eliminate squeaks and friction.

The T-plate 302 may optionally be anchored to the glove 101. The T-plate's path is limited by body guides like 202 and by band-terminating anchors 307. The anchors 307 are affixed to the glove 101 in the embodiment of FIGS. 7A and 7B. It is observed that the two anchors 307 can be placed further apart from the T-plate 302 to enhance postural control.

Figure 13A:
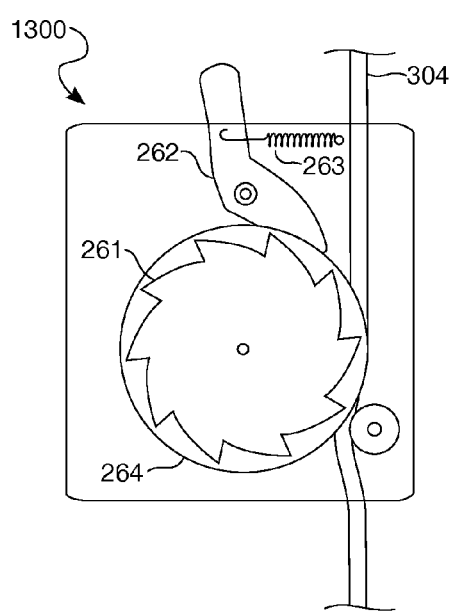
FIGS. 13A and 13B present a ratcheting band control assembly as may be used in the back support device of FIG. 12.
Figure 13B:
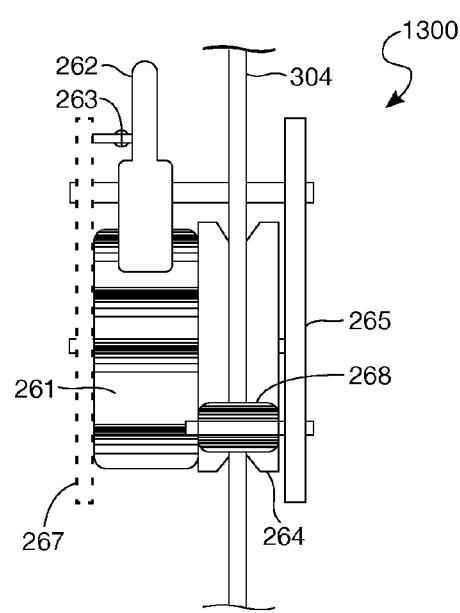

The back support device 700 also includes cable control dials 306. The cable control dials 306 may be in the form of knobs. Alternatively, the cable control dials 306 may be rotating pickup wheels (for retracting/dispensing cable as it is turned) or cable ties for a cable to be manually pulled. In another aspect, a ratcheting band control assembly may be used. FIGS. 13A and 13B present a ratcheting band control assembly 1300. FIG. 13A offers a front, or plan view, while FIG. 13B shows a side view. A front cover panel 267 is provided in FIG. 13B in dashed lines. The control assembly 1300 may serve as the dial 306. The ratcheting band control assembly 1300 includes a ratchet 261, a pawl 262, a spring 263, and a cable pick-up wheel 264. The control assembly 1300 also includes a back plate 265 and a wheel 268 used for keeping the cable in the track of the cable pick-up wheel 264. It is understood that any powered and computer-controlled cable control device with or without a mechanical advantage in its design may be used.

Figure 12:
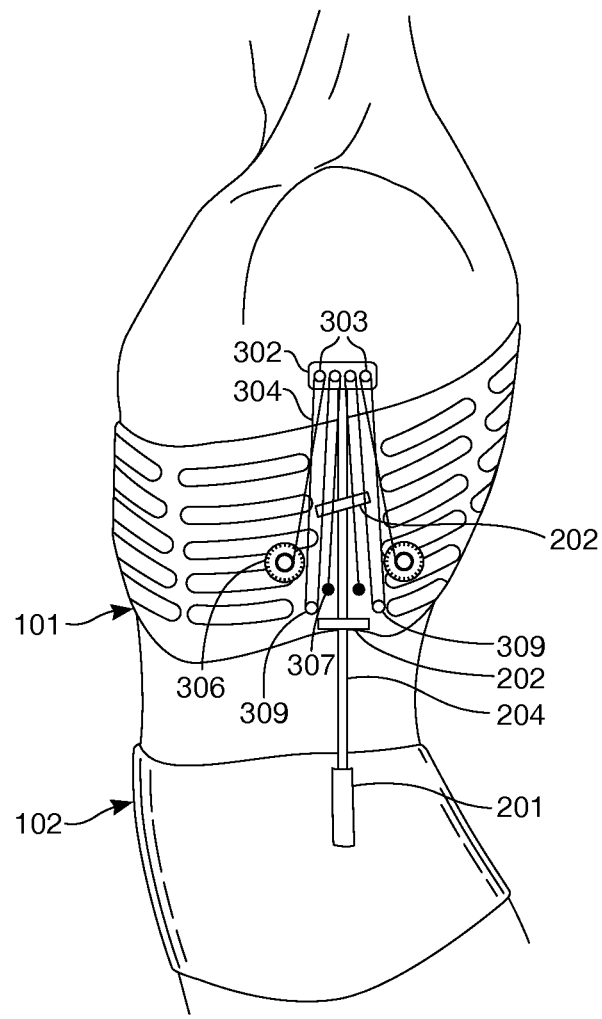
FIG. 12 is a side view of a back support device of the present invention, in still another alternate embodiment. Here, the device uses a flexible rod as a medial element. The rod cooperates with tensioning bands and a power band tensioner that is integral to the upper support component to adjust the amount of offloading that takes place.

In the cable control assembly 350 in the T-plate assembly of FIG. 12, the two anchors 307 may optionally be combined to a single insertion point. In fact, the entire array of pulleys and anchors on the T plate 302 may be shifted (elements placed further apart or closer together) to modify leverage as desirable for various applications and users. In the illustrated embodiment there is an anterior and posterior assembly (one on each side of the rod 204) each having its own dial 306, T-plate pulley 303 and anchor 307. However, a single dial, pulley and anchor is also practical and, in this case, a singular pulley 303 can be located on the T-plate.

Figure 14:
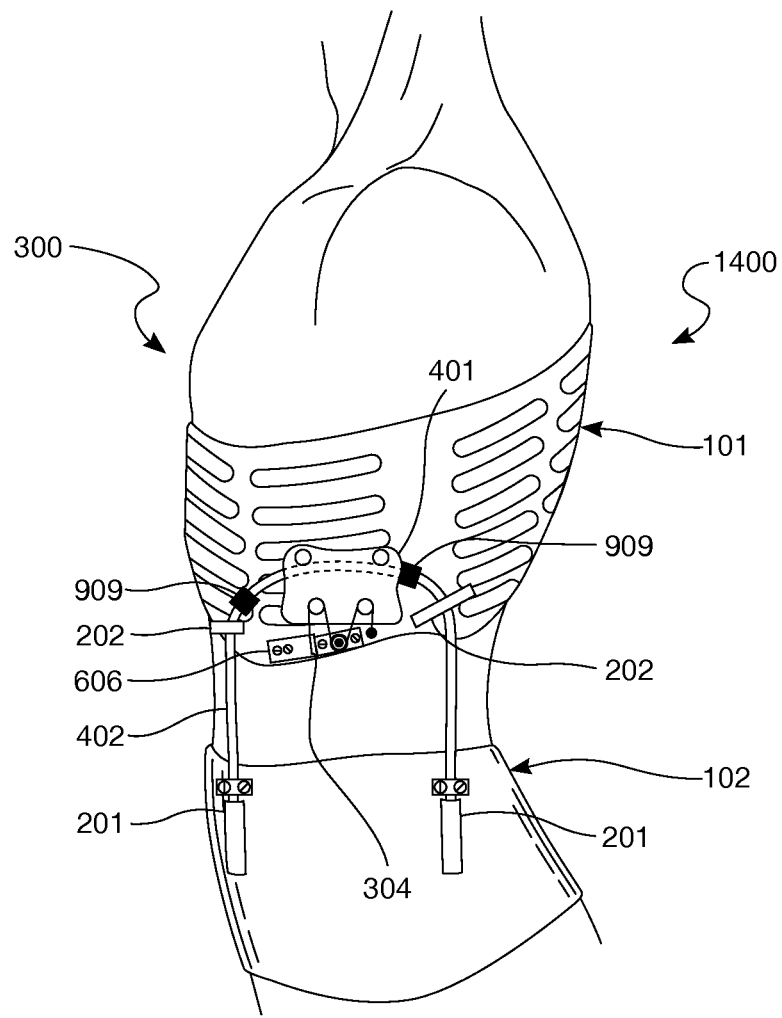
FIG. 14 is a side view of a back support device of the present invention, in still another alternate embodiment. In this arrangement, an arcuate rail is again used as a medial element. In addition, a cable control assembly resides on the upper support component. The assembly allows a tension band to be manually adjusted.

FIG. 14 is another side view of a back support device 1400, in an alternate embodiment. Here, a pulley-assisted rail and coaster assembly are provided with the upper support component 101. The assembly allows a tensioning band to be manually adjusted. This is done through the use of a cable locking mechanism 606.

In the arrangement of FIG. 14, band tensioning is controlled by the manual pulling of a band 304. After the band 304 is pulled to a desired tension, the tension is held through the cable locking mechanism 606.

The back support device 1400 employs an arcuate rail 402. The rail 402 traverses across a side of a user's torso 300. Opposing ends of the rail 402 are secured in respective holsters 201. The rail 402 is fabricated from a flexible material that permits movement of the user with only minimal resistive force. Location of the rail 402 along the side of the torso 300 is generally maintained by the use of elastic body guides 202. Additional details concerning the utility of the rail 402 and coaster 401 are provided below in connection with the FIG. 8 series of drawings.

Referring back to the FIG. 7 series of drawings, it is again observed that the back support device 700 includes a pair of dials 306. The dials 306 are part of a ratcheting band control assembly 1300. This is a more advanced approach in comparison to the cable locking mechanism 606 of device 1400. The dials 306 allow the user to control the tension of the band 304 simply by turning a pair of knobs. The bands 304 may be, for example, wires, cables, elastic bands, or polyester string. The pulley wheels 303 are dimensioned to keep the tensioning bands 304 close to the body of the user so as to minimize interference with clothing.

As the name implies, the cable control dials 306 will have different settings. This allows the user to adjust the tension of the bands 304. At one extreme, the dials 306 may be turned back to relax the band 304 tension, thereby reducing load on the rod 204. This position is shown in FIG. 7A. In this position, the back support device 700 can be easily donned. In one preferred embodiment, the upper support component 101 bends flexibly in the back as if having a vertical hinge (normally near or over the spine) and joins snugly in front, preferably with a hook and loop fastener. Since there is no significant vertical force being exerted by the medial element (rod 204) at the moment illustrated in FIG. 7A, the support component 101, or glove, can be more easily donned and doffed. In the opposite position, the cable control dials 306 selectively tighten the bands 304. This is the position shown in FIG. 7B. Note that the glove 101 in FIG. 7A is lower on the torso 300 than its position in FIG. 7B.

In operation, after fastening the glove 101 normally around the torso 300, the user begins to tighten the dials 306. As they are turned in the proper direction for elevation of the glove 101 to its torso-supportive state the tightened bands 304 exert a force that draws the glove upwards at anchors 307. Note that one anchor 307 is positioned on each side of the medial element 204, to with, one anterior anchor and one posterior anchor. In the embodiment of FIGS. 7A and 7B, the anterior dial is turned clockwise and the posterior dial is turned counterclockwise for tightening.

It is observed here that the back support device 700 provides for the use of a plurality of cable-tensioning elements that pull, via cables, the torso 300 in essentially opposing directions. In this way, selectively tightening or loosening the cables using the dials 306 increases the potential for extension or flexion of the user's torso 300. Thus, the second band ends of each band and the corresponding tensioning dials 306 are configured such that (i) turning both dials 306 in a first rotational motion in coordination with each other increases the potential for flexion in the user's torso, and (ii) turning both dials in a second opposite rotational motion in coordination with each other increases the potential for extension in the user's torso.

The anchors 307 may be formed as "insertion points" like muscles into bones so that they are nearly flush with the distal (outside) side of the glove. Where they do interact with other elements, they can be surrounded at least on the anterior and posterior by a ramp on each side which allows, for example, the rod 204, which is normally further from the center of the body than the pulleys 303, to pass over the anterior anchor 307, when the user bends forward or leans back, thus allowing more freedom of motion for the user. In this illustrated embodiment, the rod 204 is fundamentally supported not by the glove 101, but by the belt 102, thus offloading burden from the upper support component 101 to the lower support component 102. To the extent that the rod 204 bends, there is some reduction of length of vertical support which results in a little more turning of the dials to achieve a given position.

As the dials 306 turn, the band 304 is tightened. This causes the rod 204 to act upwardly against the glove 101, causing it to rise. The glove 101 is raised until a proper balanced position providing the desired amount of lift is reached. The user will then stop turning the dials 306. The rod 204 can be seen in FIG. 7B to have deformed responsive to this process. Thus, in this embodiment there is never disassembly required to don or doff since the entire back support device 700, including the rod 204 and cable control assembly 350, can stay associated with the glove 101. Fall-apart is further prevented by body guides 202 and sheathing 308 that covers the cable control assembly 350 and is anchored to the glove 101 as well as pulley wheel protective skirts (not shown).

The entire glove 101, medial element 204 and belt 102 may be treated as a one-piece garment. Thus, in the embodiment of FIGS. 7A and 7B, the one-piece "garment" includes two rods 204, with one rod being on the user's left side and one on the right. The rods in this embodiment are already associated with the T-plates 302, bands 304, pulleys 303 and further secured by body guides 202 and sheathing affixed to the most anterior and posterior edges of the glove both for protecting the swinging arms from encountering the working cable control assembly 350, and for the cosmetic value of a smoother outer surface.

The bands 304 are pre-secured by the dials 306 on the belt 102 at one end and by anchors 307 on the glove 101. Thus, when the belt 102 is hook-and-loop-bound around the user's hips, the rods 204 suspend the glove 101 to encounter the torso 300 a little below the ideal working position. All that is required then is to close the glove 101, preferably using a sternum hook-and-loop closure, and turn the dials 306 to the desired position and amount of spinal offload.

The throw distance of the T-plates 302 of the cable control assembly 350 can be favorably leveraged. This is helpful since it is desirable for the glove 101 to follow the subject's torso 300 and continue to exert support even when it is in motion. That motion, e.g., the user wearing the device 700 while bending to the right might result in a movement of the body by a distance greater than the distance that the release of curvature of the rod 204 could match. This, in turn, will cause the glove 101 to fall short in following the body motion and/or to have inadequate energy left stored in the rod 204 as curvature to exert stored energy and thus continue to offload burden.

In the device 700 of FIGS. 7A and 7B, for every inch the T-plate 302 rises (thereby releasing spring energy), the glove 101 can rise approximately two inches. This may be referred to as a "throw multiplier." The throw multiplier may be adjusted by changing the path of the cables 304, i.e., increasing pulleys 303 It is also possible to reduce the power that must be exerted by the dial 306 when tightening the bands 304. This too may be done by increasing the number of pulleys 303 to acquire mechanical advantage. Such an embodiment is demonstrated in FIG. 11, discussed below. Note also that the embodiment of FIG. 11 places pulleys 309 along the bottom of the glove 101. These lower pulleys 309 may optionally be moved to the top of the belt 102.

The favorable throw leverage allows the rods 204 to effectively exert more throw to allow the user to move around and still get supportive force from the cable control assembly 350. Inadequate throw would, when a movement exceeded the remaining extension range of the rods 204, result in both a loss of contact and support as well as irregularities in support as the shallow boundaries of contact are approached and interruptively lost.

It can also be seen by observing FIG. 7A and then FIG. 7B that by adjusting dials 306, body posture may be favorably adjusted. For example counter-clockwise rotation of the anterior and/or posterior dials 306 in the active position of FIG. 7B will, at least for a range of motion, favor flexion. Turning both dials shown in a clockwise motion in coordination with each other increases the potential for dial-guided flexion. Similarly, counter-clockwise rotation of one or both dials 306 can be used to favor or effect extension.

It is understood that there will be a minor assembly on the user's right side (the side not shown). Thus, simultaneously performing an adjustment of equal effect on the right side is used to achieve a balanced extension or flexion. Also, performing an unequal adjustment, different amounts on the different sides, can effect a lean to the left or right (e.g., tightening both dials on the right and loosening both on the left effects a lean to the left, etc.). If a North-facing user loosens the right anterior dial and tightens the left posterior dial, the support device 700 will effect a lean towards approximately the Northeast depending partially on the user's body, the position of the pulleys 303, the rod 204, and anchors 307.

The location of the pulleys 303 and anchors 307 can be adjusted to "tune" the back support device 700 to create the best mix of power and posture control for user needs. In the device 700, placement of the anchors 307 favors postural control with a larger than necessary distance between the anchors 307. Where postural control is not desired, the path of the band 304 from pulley 303 to anchor 307, will be more vertical to increase potential vertical offloading. Thus, in those embodiments, the anchors 307 may be closer together and the path of the band 304 will not need to cross itself near the pulleys 303 to accentuate the favored torque.

In addition, the anchors 307 may be relocated several inches farther apart Alternatively or in addition, the band path can proceed from the anterior left dial to the posterior pulley 303 to the anterior anchor 307 to allow more postural impact and also to provide a combination of controls that includes favoring or effecting torso rotation.

In the arrangement of FIGS. 7A and 7B, the anchors 307 are placed so far apart that, instead of being on the subject's side, are moved medially, i.e. closer to the sagittal plane of the user. This allows dial adjustments to control degree of flexion/extension, bending in other directions (where simultaneous control of potentially all dials on both sides bias motion in diagonal and other non-sagittal directions), and torso rotation. For example, in a modified FIG. 7A where the anchors 307 are moved further apart (moving them closer to the intersection of the sagittal plane and the glove 101 which on the anterior side is nearer the navel), a tightening of the left anterior dial 306, i.e. a clockwise dial rotation, plus a simultaneous loosening of the left posterior dial (clockwise dial rotation), a loosening of the right anterior dial, and a tightening of the right posterior dial can be used to rotate or favor the rotation of the torso to the left (from the perspective of the user). Reversing each of the above can be used to assist the right-wise rotation for a user.

In an alternate embodiment, a back support device may be provided which provides the desired mechanical advantage, or "lifting distraction," while also maintaining comfort to the user. In this respect, the upper support component 101 need not be placed in a state of high compression. This embodiment is particularly applicable to subjects who require substantial load offload but who don't want to fight that same offload (or compression) force to move. Such an embodiment is also appealing to those who may require a wide range of motion and minimal resistance.

Figure 8A:
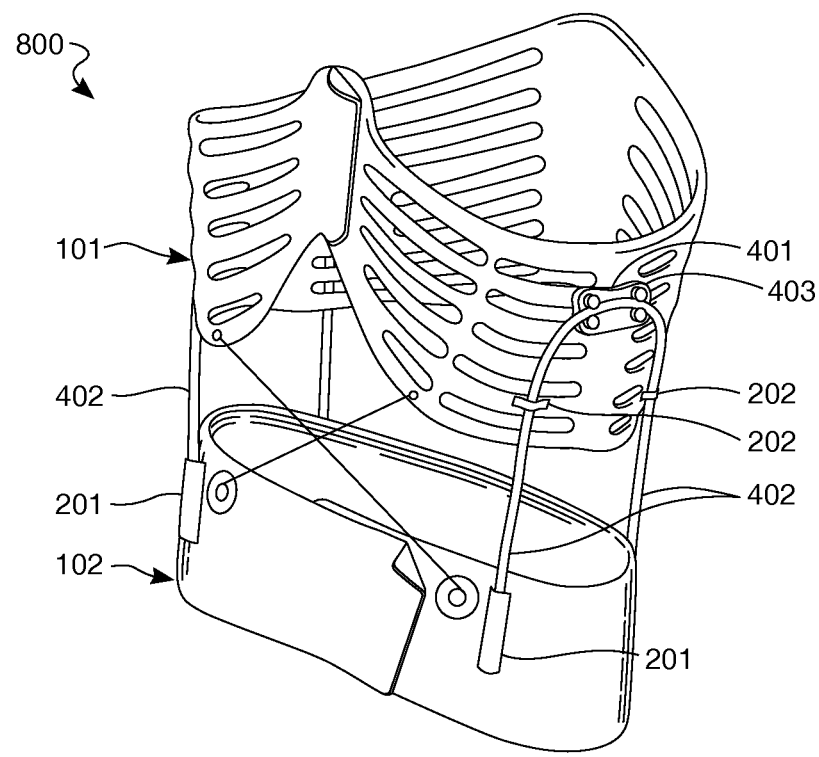
FIG. 8A is a perspective view of a back support device of the present invention, in an alternate embodiment. Here, arcuate rails are used on opposing sides of the user as the medial elements. Each arcuate rail has an apex supporting a coaster which translate along the apex for support.

FIG. 8A is a perspective view of a back support device in another alternate embodiment. The device is shown at 800. Here, a novel coaster 401 is used to apply a load from the device 800 to an arcuate rail 402, thereby offloading the upper torso burden to the lower component 102 of the back support device 800. Thus, the rail 402 serves as the medial element.

Figures 8B, 8C:
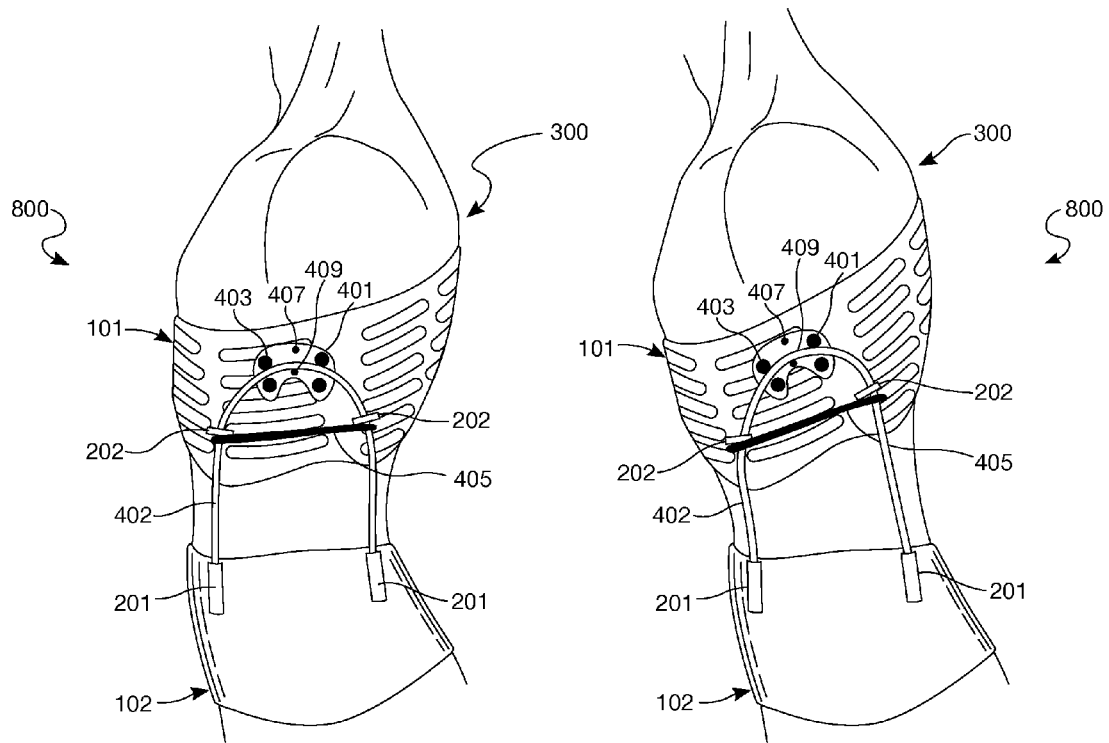
FIG. 8B is a left side view of the back support device of FIG. 8A. The device is being worn by a user. Here, the rail's radius of curvature is restricted by a loop.
FIG. 8C is yet another side view of the back support device of FIG. 8A, having the coaster, the rail and the loop. Here, the torso of a user is in partial flexion. Body guides provide limits to the travel of the arcuate rail.

FIG. 8B is a side view of the back support device 800 of FIG. 8A, in a slightly modified embodiment. Here, the device 800 is being worn by a user. Of interest, a radius of curvature of the rail 402 is restricted by a loop, or band 405. The loop 405 limits the effective radius of the upper portion of the rail 402.

The rail 402 defines a loop having first and second ends. The opposing ends reside in holsters 201 affixed to the belt 102. Rails 402 are placed on each of the left and right sides of the belt 102.

Each rail 402 is preferably a flexible and deformable element, such as a fiberglass or a carbon rod, or an assembly of thin carbon rods that are bundled. A suitable rod will have a small radius (e.g., between 1.5 and 2 mm when round rods are used) laminated with a strong (e.g., 90 Durometer shore A) urethane or other flexible material. The use of thinner rods permits a smaller radius of curvature for the rails 402 while the combination thereof enables more support.

The rails 402 are connected to the glove 101 by means of body guides 202. Two or more guides 202 may be used for each rail 402. The holsters 201 and guides 202 create an arching profile for the rails 402. Hence, the referenced radius of curvature. Each rail 402 also has an apex between the first and second ends.

To further support and guide the rails 402, coasters 401 are provided. Each coaster 401 is positioned on the upper support component 101. More specifically, one coaster receives a rail 402 on a left side, and the other coaster 401 receives a rail 402 on the right side. Each coaster 401 has a plurality of rollers 403 that closely receive a respective rail 402 proximate its apex, allowing the coaster 401 to roll over the rail 402.

The rail 402 in FIG. 8A passes between upper and lower rollers 403 of the coaster 401. However, it is not necessary for the rail 402 to contact the lower rails. Although the lower two rollers are not mandatory for operation, they serve both as lower securing agents for the coaster facings and to protect and confine the rail 402 during operation.

The rail 402 may also include, in whole or in part, more than one layer. For example, a single band of three rods may be used. Where the rollers 403 engage the rail 402, this alignment of the rods can provide a three-rod wide flat "road" for the rods to ride. Though a user with a wide upper torso, for example, can bend the rail 402 distally so that the rollers 403 may not perfectly engage the rail 402, the force of the rollers 403 tends to align the rail 402 at actual points of contact.

Referring to the loop 405 in FIG. 8B, the loop 405 is also used to control the stiffness of the rail 402 and to attenuate the distance between the lower vertical portions of the two rail ends before they enter 201 the holster. The loop 405 may be elastic or inelastic. In one aspect, a hook and loop material may be used for the loop 405. This has the advantage of being easily adjusted. The loop 405 may be anchored to the glove 101, the rail 402 (at contact points as shown in FIG. 8B) and/or body guides 202, to produce the desired limits both on radius and rail travel under load-induced deformation.

FIG. 8C is yet another side view of the back support device 800 of FIG. 8A The device 800 again includes the coaster 401, the rail 402 and the loop 405. Here, the torso 300 of a user is in partial flexion. User guides 202, or tabs, beneficially provide limits to the travel of the rail 402.

In the embodiments illustrated in FIGS. 8B and 8C, the loop 405 is attached to the rail itself below the body guides 202. Where the band 405 is sufficiently broad, it need not be affixed with a clamp, glue, etc. to the rail itself. For example, in testing with a 1.5 inch wide strip of hook and loop material (having about one half of the length as hooks and the other half as loops on the opposite side and opposite end forming the typical loop-cinching strip application) the loop 405 was easily adjusted by loosening or tightening tension. Beneficially, the friction between the loop 405 and the rail 402 kept the loop 405 effectively in position. However, connecting the loop 405 at one end to the rail 402 provides longer-term positional stability without compromising the ease of hook and loop adjustment to adjust the tension.

Alternatively, the loop 405 may be attached to the glove 202 at the center. In embodiments where the band 405 is attached to the glove 101, the band 405 will move with the torso 300 at that point.

It is also noted that by tightening the loop 405, the stiffness of the rail 402 to vertical load is increased responsive to the decreased upper radius. Also, the position of the apex of the rail 402 is adjusted by the loop 405, which can be used to adjust the vertical position of the glove 101. For example, the loop 405 can be tightened by the user to increase the vertical position of the glove 101 after some slippage has occurred and/or to increase the relief for a spine receiving less support from day-worn muscles and that has become more compressed as the day proceeds.

FIG. 9A is an enlarged front view of the coaster 401 of FIG. 8A, in one embodiment. FIG. 9B is a right side view of the coaster 401 of FIG. 9A. FIG. 9C is an exploded right side view of the coaster 401 of FIG. 9A. Friction with the rail 402 is reduced by making the rollers 403 bearing-enabled and having the roller's bearings (not shown) turn on a smooth, hollow and cylindrical liner 802. The liner 802 itself is secured by pins 801 shown here as screws passing inside the liner 802, with the liner inside the bearing roller 403. The pins 801 terminate in the threaded rightmost panel of the coaster 401. Although not shown in FIG. 8B, a cover plate, shown in FIG. 9C as the leftmost panel 401, may be attached over the coaster components 802 and 403, preferably shaped like the outer perimeter of the coaster 401 and attached with screws over the coaster 401.

As the user bends forward, the coaster 401 rolls on the upper rollers 403, along the rail 402 while continuing to partially deform the rail 402 with offloaded force. The coaster 401 in FIG. 8B is attached to the glove 101 by a single pin 407, whose location can be different than as shown responsive to embodiment geography and body characteristics. The pin 407 attachment of the coaster 401 to the glove 101 allows the coaster 401 to swivel at least within a tolerance to follow the rail 402, as the subject bends forward as seen in the positional change between FIGS. 8B and 8C. In other embodiments this pin 407 is not required.

Figure 8D:
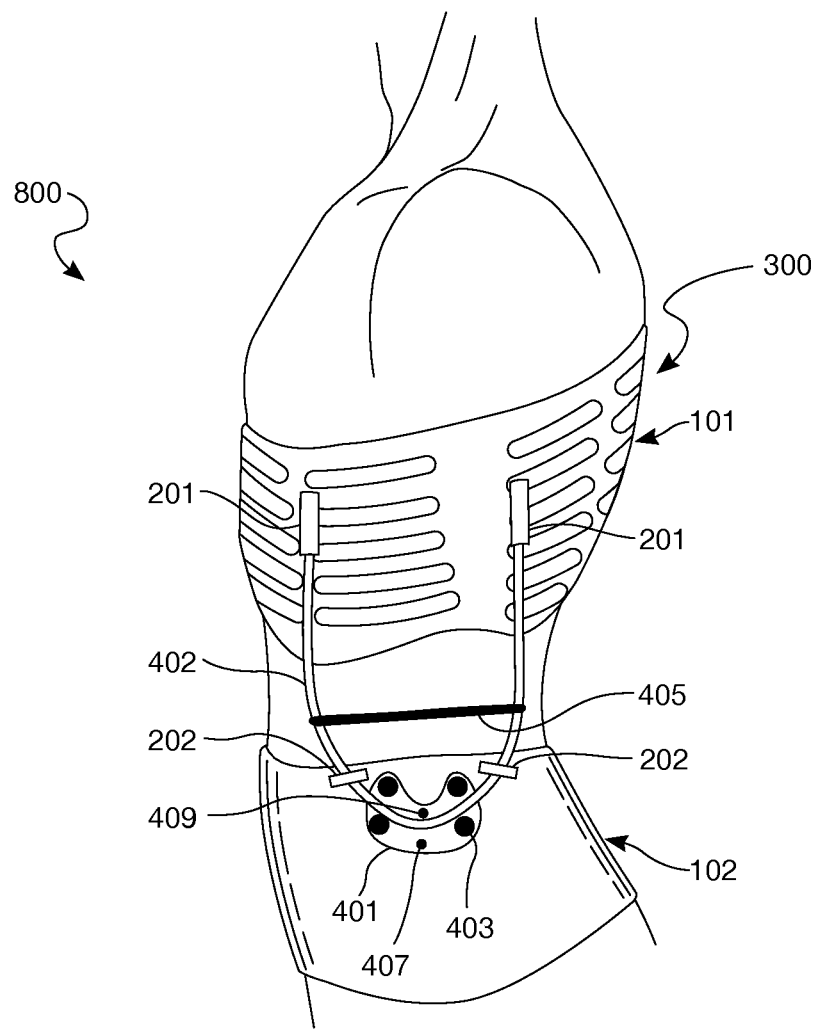
FIG. 8D is another side view of the back support device of FIG. 8A, but in an alternate arrangement. In this view, the coaster and body guides are attached to the lower support component, or belt.

FIG. 8D shows another side view of the back support device 800 of FIG. 8A, in a modified embodiment. Here, the coaster 401, the rail 402 and the loop 405 are inverted. In this view, the device 800 has been inverted by attaching the coaster 402 to the lower belt 102. In this embodiment, the coaster 401 is attached to the lower component, or belt, 102 while the rods 402 are attached to the upper component, or glove, 101 at the holsters 201. This arrangement shifts the axis of rotation. This particular embodiment possesses a loop 405 adjusting the effective structural properties of the rod 402. It should be understood that the loop 405 may be present or absent depending upon the support and motion characteristics desired.

Other grouping elements also serve to both control potentially un-grouped medial elements and reduce friction to make body action fluid and silent. For example, as the body flexes and extends, the body guides 202 slide over parts of the rail 402. In one embodiment, Teflon® tubing covers the rail 402 at these locations and the body guides 202 themselves are also lined with Teflon®. Thus, the Teflon® tubing over the rail 402 at body-guide 202 friction points provides friction and noise reduction for bound bands 405 while also being useful for grouping a plurality of individual medial elements (e.g., un-banded rods) during activity with minimized friction against the body guides 202 which, in the preferred embodiment, are also made of or are lined with low friction material.

It is desirable to protect the rails 402 at the entrance point to the holsters 201. It is observed that this can be a high-force point. For example, to encourage a larger radius of rail curvature at such points, an enlarged aperture entrance (curved or otherwise shaped to allow graduated curvature at the entrance), or a lined entrance area (e.g., with a flexible material or layer to allow graduated curvature rather than a sharp edge at the entrance), or a pin assembly can also be used to prevent too small a radius of curvature at the entry point of the holster.

Figure 8E:
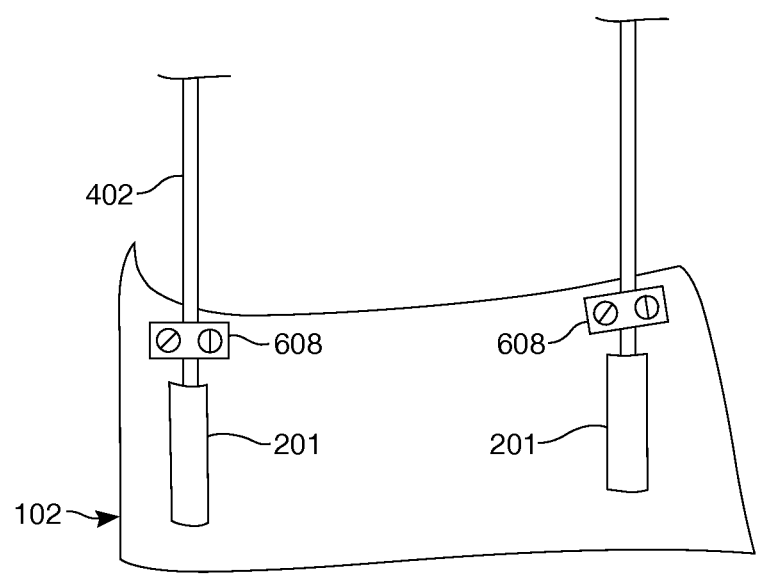
FIG. 8E is an enlarged side view of the lower support component, or belt, of FIG. 8A.

FIG. 8E is a side view of the lower support component, or belt 102, of FIG. 8A. This is an enlarged view showing a pair of holsters 201. Each holster 201 receives an end of a rail 402 (or medial element) at an entrance point 207. To reduce stress at the entrance points 207, fasteners 608 have been secured to the rail 402 just above the two entrance points 407. The fasteners 608 are also used to bind the rail 402 from axial (essentially up and down slipping) and lateral travel by tightening screws to draw the fasteners 608 against the belt 102. Alternatively or in addition, fasteners 608 may bind the rail 402 to points along the glove 101, although it is strongly preferred to just use the body guides 202 along the glove 101.

Although the embodiment of FIG. 8E restricts rotation of the distal ends of the rail 402 in planes essentially parallel to the sagittal plane at the holsters 201 with both the shaped aperture path of the holster 201 and the fasteners 608 near the top of the belt 102, another embodiment permits more rotation at these distal rail ends with a holster that is in the form of a pin. In this embodiment, which provides options for different rail-performance characteristics, particularly in the limited range or absence of fasteners 608, the holster 201 can behave, at least within a desired degree of permitted rotation, like a pin essentially normal to the surface of the glove 101 which passes through a terminal end of the rail 402, thus allowing some sagittal rotational freedom for the distal (terminal) ends of the rail 402. Various pin configurations known by those skilled in the field (including those with limited rotational ranges and configured resistances, etc.) are known, but one exemplary embodiment can be seen simply as the holster, 201, not as a part of the structural material of the outer wall of the glove but being pinned to it.

The holster 201 of FIGS. 4D and 4E, discussed above, may also be used. In FIG. 4D, the holster 201 can be seen to have a slot to allow an inferior end of the rail 402 to be inserted. Securing elements, like fastener 608, are preferably attached near the top of the belt 102. Also, in a preferred embodiment, the rail 402 is stronger (e.g., in this drawn embodiment, thicker) in the relatively straight, lower parts of the rail. This is particularly helpful for taller users where the vertical support path to the load-bearing arch may be long and helps provide support at the holster insertion point 407.

The pinned connection 407 allows the coaster 403 to follow the positional change of the torso and to simultaneously rotate such that the rollers 403 continue to engage the rail 402. However, alternative pin locations are applicable and useful. For example, it can be pinned below the rail e.g., at 409 where it will continue to follow the torso. Implementers may even choose to anchor, rather than pin, at points 407 and/or 409. The rail 402 will normally be configured to continue to be deformed even as the user is bending forward so that it still exerts a supportive force but its deformation shape changes based on degree of flexion, position and width of body-guides, and force on the coaster 401 from the glove 101. The body-guides 202, or tabs, limit the lateral travel and deformation of the rail 402 to a desired shape that favors easy extension to follow trunk flexion appropriate for the individual user's body. The body guides 202 not only keep the rail 402 close to the glove 101 but are the end determinant of limits of rail curvature shift. Note in FIG. 8C that the top right portion of the rail 402 has been warped upwards and rightward by the off-center and burdening coaster 401 but the right body guide 202 has prevented further rightward motion of the rail 402 because too much would make the return trip of the coaster 401 (torso extension) more difficult.

In the preferred embodiment, the rail 402 deforms and stores energy due to the downward force exerted on it ultimately by the glove 101 rather than depending on medial element support adjustments (such as 1005 and 306 in FIG. 10B) for providing continuity of burden offload. This allows stored energy in the rail 402, an exerted lifting force to the glove 101, and tolerance of user motion. Note that if the user moves in a manner that causes the glove 101 to move away from the rail 402 (for example, sitting up after slumping), the rail 402 can "un-deform" upwards to continue to provide uninterrupted contact and support. An active user may require more deformation than some embodiments make room for both for increased energy with lift and continuity of support. Thus, choosing the rail diameter, material and the radius of the upper rail is a desirable step in ensuring adequate throw distance (the magnitude of distance that the coaster-contacting portion of the rail can move the coaster by undeforming).

The coaster 401 will, as the subject bends, follow and continue to deform the rail 402 within body guide 202 and other applicable limits without requiring the user to overcome the lift that was intended to be a benefit, not a burden. The radius and center placement of the roughly semi-circular upper-anterior portion of the rail 402 upon which the coaster 401 rides (from the position shown in FIG. 8B to a position closer to the one shown in FIG. 8C) follows a path not too unlike a circle. Dotted line 503 generally charts a radial path of rotation.

The coaster 401 in FIGS. 8A through 8E, is, in other applicable embodiments, further combinable with concepts described for the T-plate 302 and rod 204 embodiments of FIGS. 7A and 7B for the additive benefit of improved throw distance, favorable leverage, leverage-enhanced control of body position in any direction, and easy adjustment of equipment over time. Thus, it is possible to combine the back support device embodiments of the FIG. 7 series (device 700) with the back support device embodiments of the FIG. 8 series (device 800). This means using both the pulleys 303 and the coaster 401, but not the rod 204.

Figure 10A:
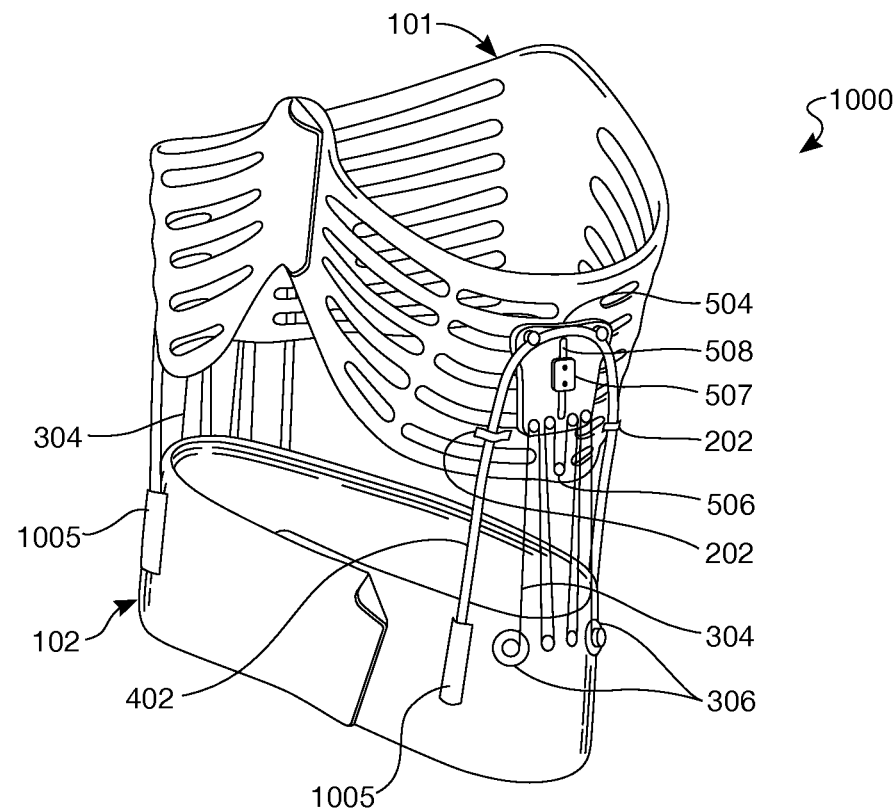
FIG. 10A is a perspective view of a back support device of the present invention, in an alternate embodiment, Here, an arcuate rail is again provided as a medial element. In addition, a cable control assembly is shown connecting the upper and lower support components.

FIG. 10A is a perspective view of a back support device, in still another alternate embodiment. The device is indicated at 1000. Here, arcuate rails 402 serve as medial elements. The rails 402 are shown connecting upper 101 and lower 102 support components. In addition, a cable control system 350 is provided.

Figure 10B:
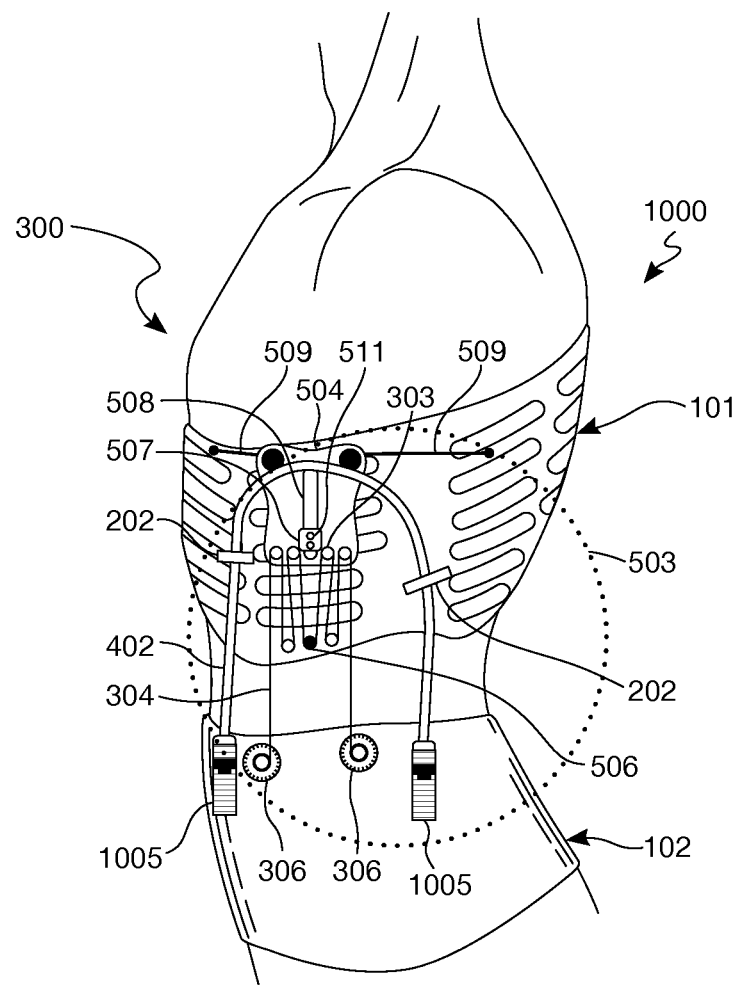
FIG. 10B is a side view of the back support device of FIG. 10A, with the device being shown on the torso of a user. The cable control assembly is seen with rail elevation controls.

FIG. 10B is a side view of the back support device 1000 of FIG. 10A Here, the device 1000 is shown on the torso 300 of a user. The cable control system 350 is seen with rail elevation controls, or coaster 504.

Figure 10C:
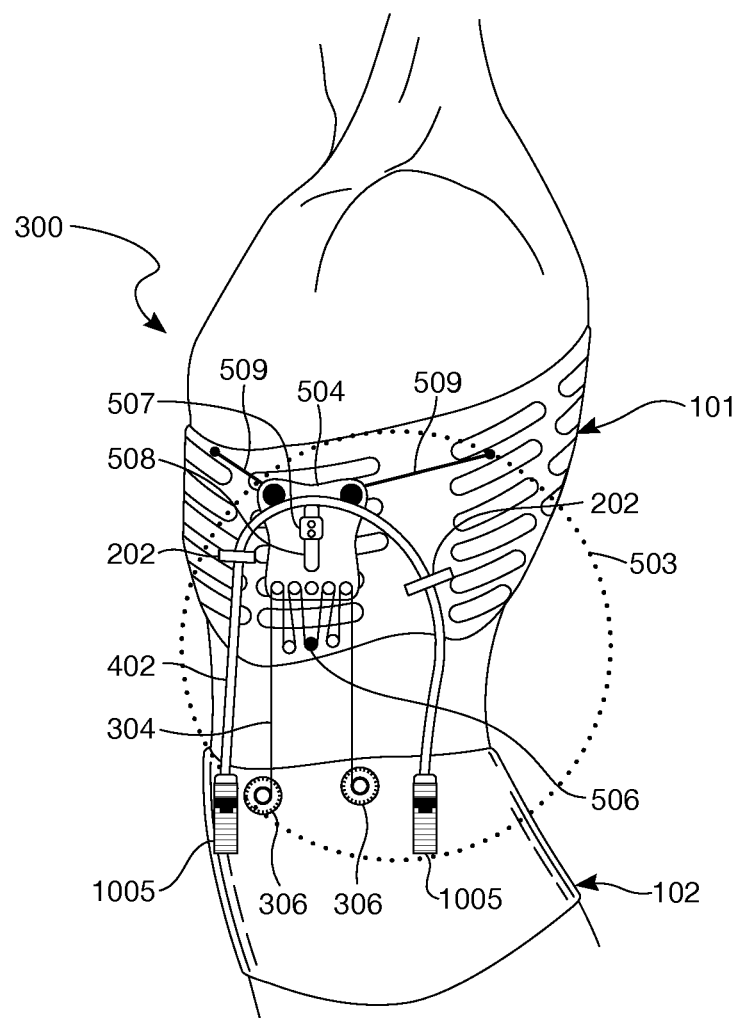
FIG. 10C is another side view of the back support device of FIG. 10A, with the device again being shown on the torso of a user. The user is an upright position with the coaster at the apex of the rail.

FIG. 10C is another side view of the back support device 1000 of FIG. 10A, with the device 1000 again being shown on the torso 300 of a user.

Figure 10D:
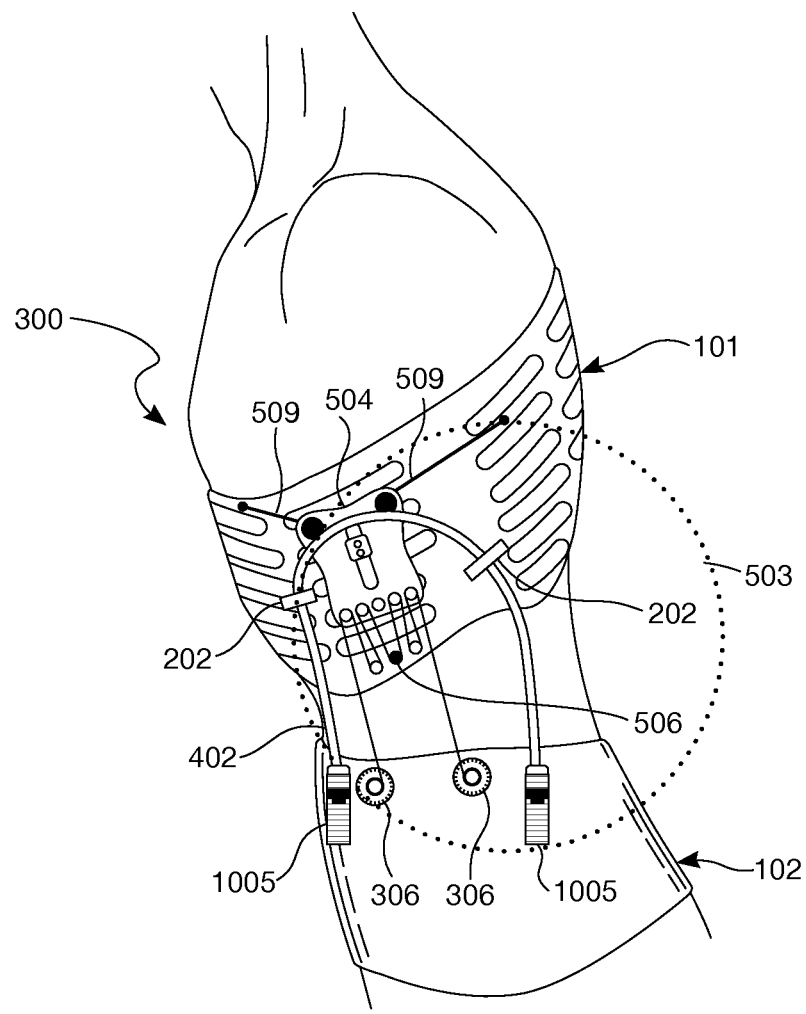
FIG. 10D is another side view of the back support device of FIG. 10A, with the device again being shown on the torso of a user. The torso is in partial forward flexion.

FIG. 10D is yet another side view of the back support device 1000 of FIG. 10A, with the device 1000 again being shown on the torso 300 of a user. The torso 300 is in partial flexion.

In the arrangement of FIGS. 10A through 10D, pulley wheels 303, anchors 506 and tensioning band 304 are again used. Anchors 506 are used to support the tensioning band 304. The rail 402 replaces the rods of FIGS. 7A and 7B. The single pin 407 of FIGS. 8A through 8D has been optionally replaced by a coaster control assembly, 507 and 508. The coaster control assembly 507/508 serves to:

a) keep the coaster 504 close enough to the body to be out of the way of the user's arm,
b) stabilize the action of the coaster 504 whose connections to anything else are, in some embodiments, limited to the rail 402 at the upper wheels 403 and the cable control assembly 350, and
c) optionally, to provide rotational force upon the channel (508, a slot cut into the plate of the coaster 504).

Various methods may be used for accomplishing the above objectives. These include:

a) The use of vertically-arrayed pins in the channel (these can be seen as the two circles in the slider 507).
b) The use of a low-friction sliding element, normally "H" shaped, and
c) The use of so-called tow ropes.

Pins

First, a pair of pins 511 may be provided. The pins 511 have a bearing cylinder around each of them to minimize friction and to reduce incumbent noise. The pins 511 reside in a plate 507. The plate 507, in turn, slides along a channel 508 in the coaster 504. The pins 511 are shown in the FIG. 10 series as being essentially vertically arrayed in the plate 507. It is preferred that at least two adjacent pins 511 be used. This is because when the body rotates e.g., in flexion (seen in FIG. 10D), the pins' rotation exerts a rotating force upon the channel 508 of the coaster 504, which encourages the coaster 504 to rotate in a direction (here drawn as counterclockwise in flexion) favorable to the coaster 504 following a least-resisted path.

The pins 511 are screwed into or otherwise bonded to the glove 101. They will, for convenience, be described here as screwed into the glove 101 at reinforced points. The pins 511 are inserted through the holes in the sliding plate 507 with the heads of the pins 511 being larger than the holes in the plate 507. Thus the plate 507 is loosely secured against the distal (to the body) side of the base plate of the coaster 504. The pins' heads secure the moving rectangular plate shown in 507 which, in turn by acting as a washer over the channel 508, assures that the coaster 504 does not stray too far from the torso 300.

A first tolerance of the plate 507 and pin 511 arrangement regards how far the plate 507 can move away from or closer to the torso 300 on the pins 511 as the plate 507 slides up and down the channel 508 responsive to upward and downward movement. This tolerance is optionally spring resisted. For example, a compression spring around each pin (or outside each optionally associated bearing cylinder) between glove and plate will exert a force on the plate 507 away from the user's body. A washer (not shown) between the proximal side of the base plate of the coaster 504 and the spring, whose diameter is wider than the width of the channel 508 is preferably added to provide a smooth action. By providing more pin length than the minimum needed, a spring-mediated tolerance is effected to accommodate some irregularity and non-planarity in the path of the coaster 504.

A second tolerance is for coaster weaving (or yaw in the path of the coaster 504 on the rail 402, i.e., where the coaster 504 has a rotational axis normal to a transverse plane) thus allowing the coaster 504 to rotate within a tolerance responsive to user action so that the coaster 504 can comfortably follow the not-perfectly-planar path of the coaster 504 in, for example, flexion (see FIG. 10D). This is helpful since, in a significant number of applications, the rail 402 itself will not entirely exist in a single plane while the holsters 201, or elevation controls like 1005, may be shifted medially (here, towards the sagittal plane) in order to stay a little closer to the torso 300 to minimize interference to motion.

There are several ways to manage this second (carrier yaw) tolerance. These include:

1) The flexibility of the rail 402 itself provides its own tolerance by deforming to meet the coaster 504.
2) The distance between the baseplate of the coaster 504 and the coaster cover (not shown) that encases the other coaster and pin elements limits weaving (where the width of the rail components is near that of the space in the coaster to contain it). The less free room in the coaster for the rail, the less weaving tolerance).
3) The first tolerance. (The spring assembly also provides a tolerance for coaster yaw.)
4) The body guides 202 as they determine the curvature of the rail 402.
5) The difference between the diameter of the pins 511 (including any bearing layers) and the width of the channel 508.

However, in the preferred embodiment, all of the above elements may be used together as needed to effect a tolerance control that can be "tuned" to vary as needed to best accommodate a variety of user body types.

Sliding Element

Second, a low-friction sliding element may be used. In this respect, the plurality of pins 511, the rectangular plate 507 (including a washer) may be replaced by a single piece, e.g., a rectangular slider having a height and width similar to the area taken up by the assembly 507/508. A preferred rectangular slider element to use in place of plate 507 is a familiar "H" shaped low-friction nylon part with the left and right sides of the channel 508 being inserted into the slots of the "H," allowing for essentially vertical travel of the slider in the channel 508. Even though the slider can be bonded directly to the glove 101, the preferred attachment is a pair of screws or pins positionally analogous to the pin 511 option described above so that the above-mentioned spring and gap-enabled tolerances are still enjoyed (thus becoming a hybrid of the spring-loaded pin-pair and the simple anchored rectangular slider). Here, the tolerance that had been effected by pin diameters being less than the diameter of the width of the channel 508 becomes the space between the diameter of the pins 511 and the holes for the pins in the slider material.

Tow Ropes

Third, the pin-and-groove assembly 507/508 may be replaced (leaving only the coaster plate and pulleys on the coaster 504) or cooperatively assisted by other practical approaches for causing the coaster 504 to travel with the glove 101 (and thus the user's body) and yet not unduly restrict the movement of the coaster 504. One of many such approaches is a plurality of bands 509, or "tow ropes," as shown in FIG. 10B. The bands 509 are attached distal to the coaster 504 to the glove 101. When the torso 300 flexes or extends, these pull the coaster 504 essentially forwards (left in the drawing) or backwards respectively with a favorable torque for reduced resistance to travel.

One process for this is merging a rubber or other elastic agent with a loosely woven fabric. When the threads of the woven fabric itself are pulled tight, the elastic mediated expansion is largely ended. Thus, it can behave like an elastic band with essentially hard limits. As can be seen between the positions of FIGS. 10B and 10C, even a slight elasticity allows the elevation of the glove 101 in donning but, in FIG. 10C, the approaching and ultimately essentially hard limits of further stretching will cause the cords 509 to pull the coaster 504 forward in flexion and backwards in extension.

It is noted that in the back support device 1000 of the FIG. 10 series of drawings, the single anchor 506 may be replaced by two anchors, where a first anchor moves towards the front responsive to the anterior dial, and a second anchor moves towards the back responsive to the posterior dial. This is similar to the positions of the anchors 307 in FIGS. 7A and 7B. This, of course, would be done on both the left and right sides of back support device 1000. Thus, the band 304 from anterior dial 306 terminates anterior to the dial 306, and the band 304 emanating from the posterior dial terminates (attaches to the glove 101) posterior to the drawn position. When the two anterior dials (one on each side of the user) 306 are rotated clockwise (tightening the anterior band 402) and/or the posterior dial shown is rotated clockwise (loosening the posterior band), the glove 101 is favored for extension. Doing so (tightening the anterior band and loosening the posterior band) on both sides, similar to the discussion of FIGS. 7A and 7B, makes for a more balanced extension while a reversal of the dial rotations favors flexion.

In the back control devices of the FIG. 7 series of drawings (device 700) and in the FIG. 10 series of drawings (device 1000), bands or cables are used in conjunction with medial elements. The tensioning bands 304 extend between the upper 101 and lower 102 back support components. However, the tensioning bands 304 may be used in other pulley arrangements.

Figure 11A:
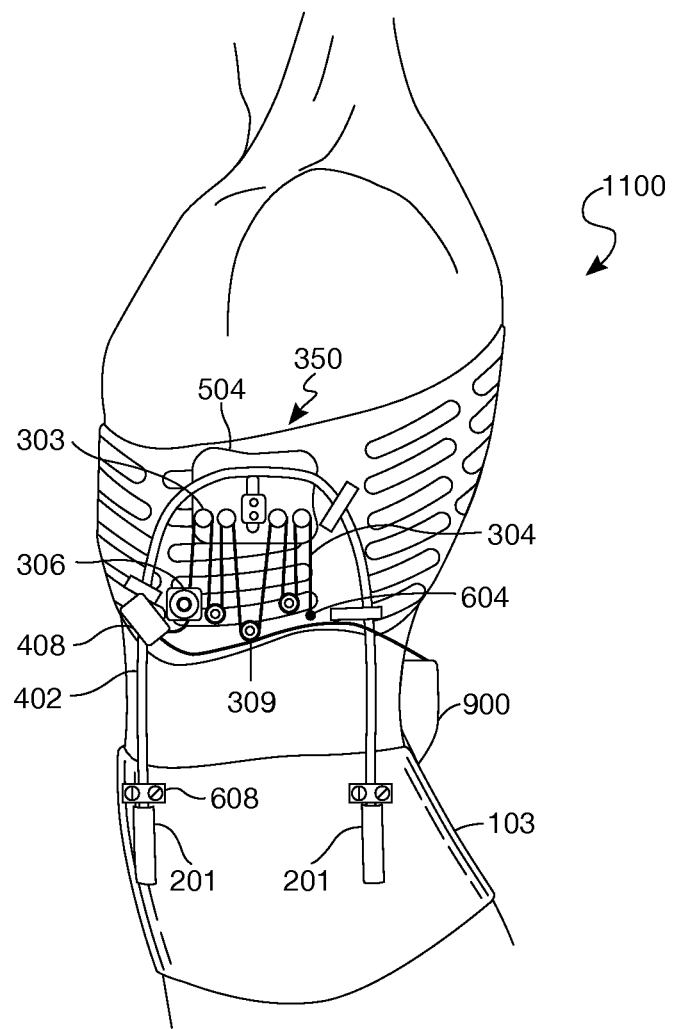
FIG. 11A is a side view of a back support device of the present invention, in still another alternate embodiment. Here, an arcuate rail is again used as a medial element connecting the upper and lower support components on each side of a user. In addition, a cable control assembly is shown along with a powered band tensioner. The tensioner is driven by an onboard controller.

FIG. 11A is a side view of a back support device, in still another alternate embodiment. The device is indicated at 1100. Here, arcuate rails 402 are again used as medial elements. The rails 402 connect the upper 101 and lower 102 support components. In addition, a cable control (or pulley) assembly 350 is shown. The cable control assembly 350 includes a powered band tensioner 408. The novel powered tensioner 408 is driven by an onboard controller.

Figure 11B:
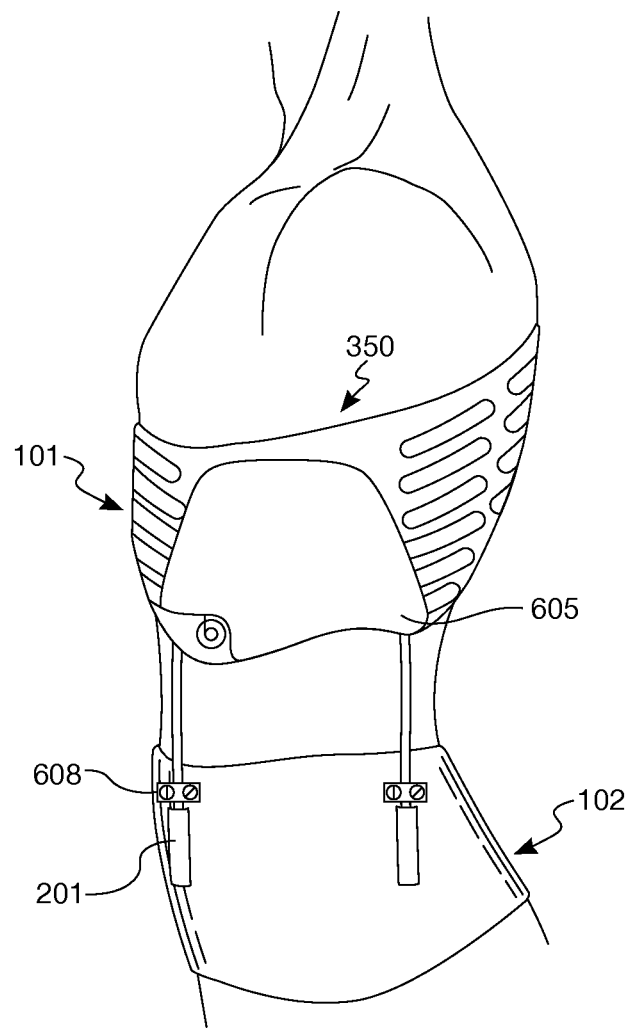
FIG. 11B is another side view of the back support device of FIG. 11A. This view illustrates the optional use of a protective cover over the medial elements.

FIG. 11B is another side view of the back support device 1100 of FIG. 11A. This view illustrates the use of a protective cover 605. The cover 605 is preferred, as it keeps clothing and fingers from getting tangled with the tensioning band 304.

The device 1100 of FIGS. 11A and 11B illustrate a cable control assembly 350 essentially limited to the area of the glove 101. Here, the tensioning cable 304 connects the coaster 504 with a lower cable control dial 306, which in turn is anchored to the glove 101. For example, when the tensioning cable 304 is pulled downward, it passes through a hole in the lower cable control dial 306. A threaded hole exists adjacent a passageway in the dial 306. As the dial 306 is turned, tension in the cable 304 is adjusted.

Figure 15A:
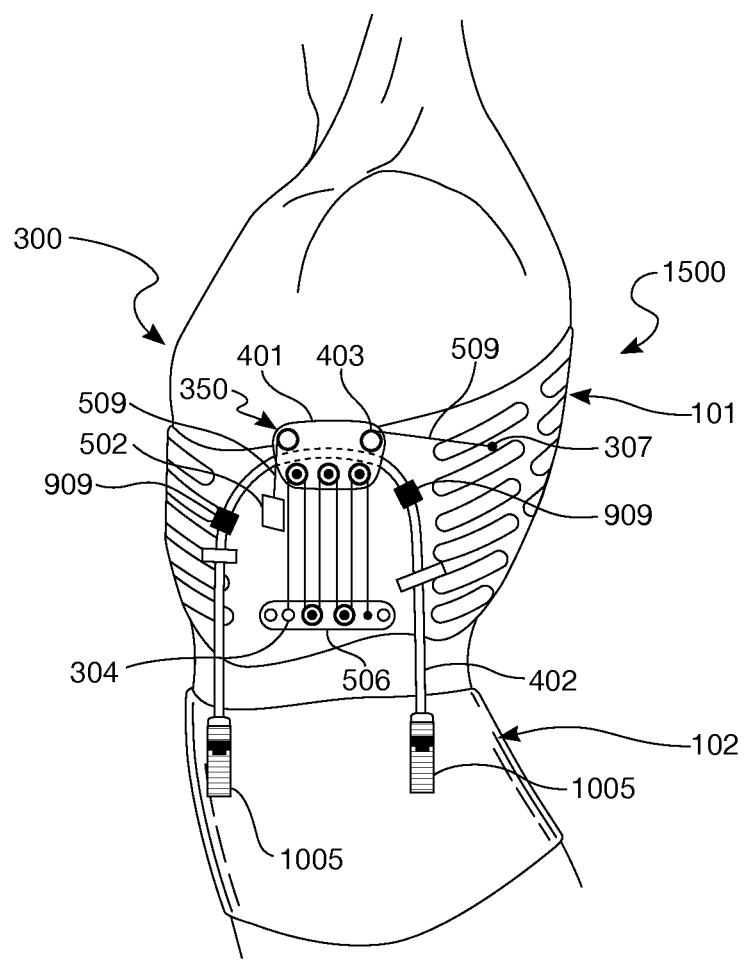
FIG. 15A is a side view of a back support device of the present invention, in yet another embodiment. The support device is again presented on an illustrative torso. In this embodiment, an arcuate rail is provided as the medial element. In addition, a cable control system having a tension band is provided. Also, a controller is provided for monitoring band tension.
Figure 15B:
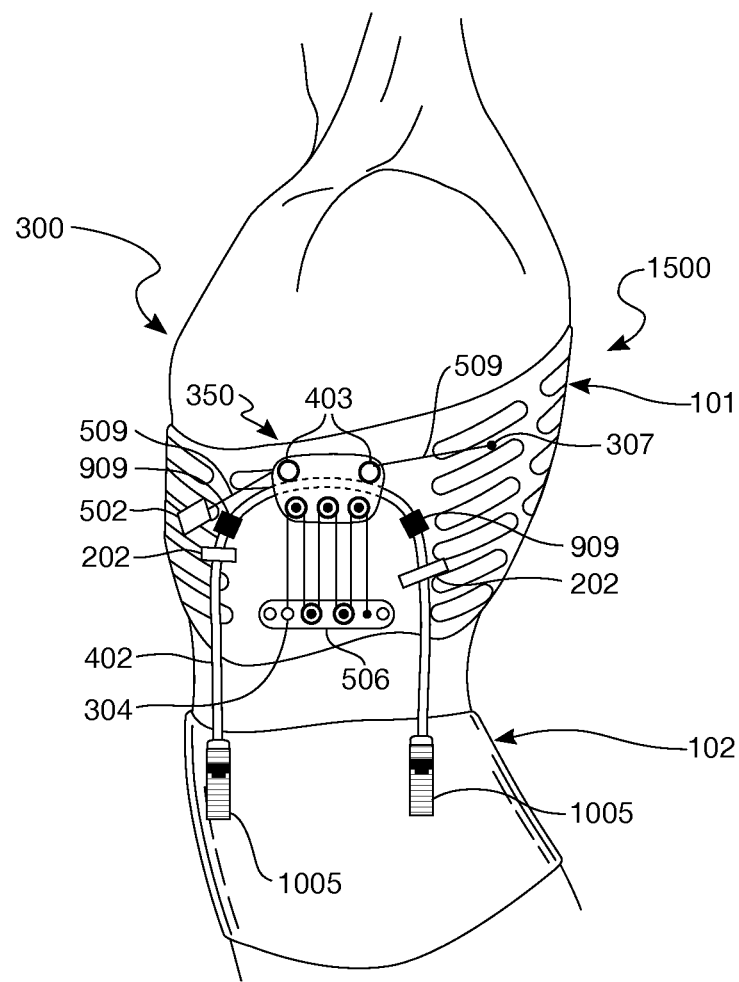
FIG. 15B is a side view of the back support device of FIG. 15A, showing the tension band having been tightened. The upper support component is thereby lifted on the user's torso.

Tensioning the cable 304 results in the change illustrated, for example, between FIGS. 15A and 15B. FIG. 15A is a side view of a back support device 1500, which utilizes an arcuate rail 402 and a coaster 504. In addition, the device 1500 uses a tensioning band 304 and a controller 502. The dial 306 and the controller 502 are part of a cable control assembly 350, which is confined to the upper support component 101.

Figure 15C:
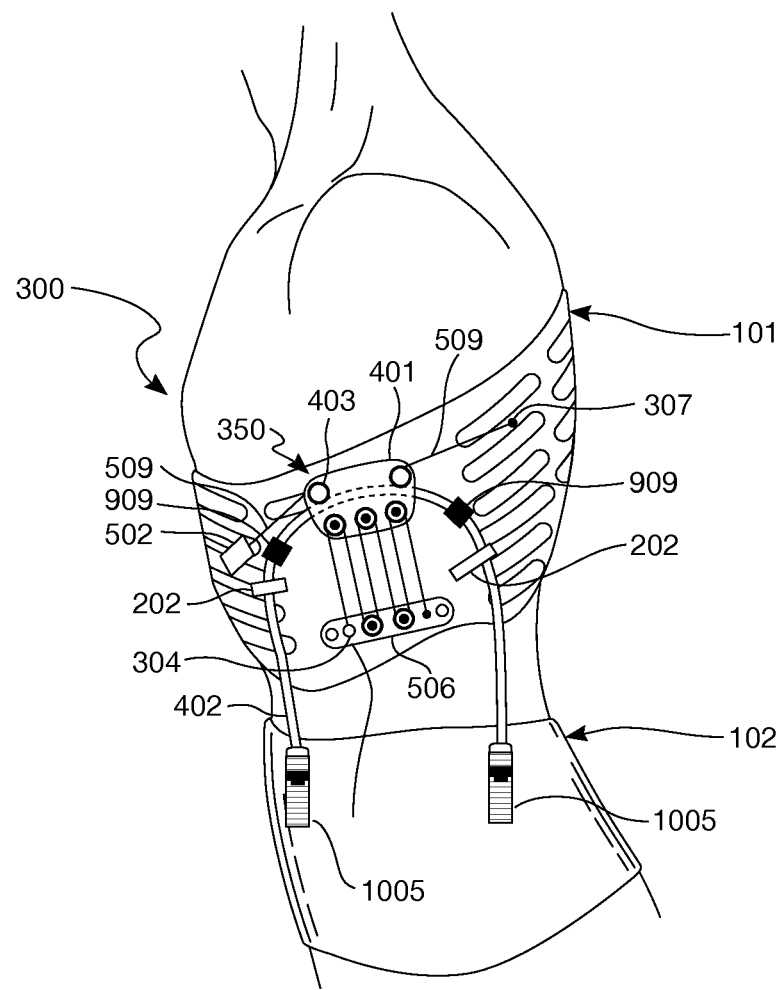
FIG. 15C is another view of the back support device of FIG. 15B. Here, the torso is in partial forward flexion.

FIG. 15B is a side view of the back support device 1500 of FIG. 15A. Here, the tensioning band 304 has been tightened. Holsters 1005 are seen receiving the arcuate rail 402. The torso 300 is in an upright position. FIG. 15C is another view of the back support device 1500 of FIG. 15B. Here, the torso 300 is in partial forward flexion.

As the cable 304 is pulled, this closes the gap between the glove-anchored cable control assembly and the essentially glove-unconstrained coaster 401. This, in turn, pulls the glove 101 upward through the glove-attached cable control assembly 506 against the supporting rail 402, which offloads torso burden to the belt 102. The tension in the cable 304 is multiplied by the plurality of pulley runs, making it easier for the user to create significant lift on the upper support component 101 with lesser tension on the cable 304. This exemplary cable pulling example will, in many applicable embodiments, be replaced by cable pulling powered actuation, preferably anchored to the glove near the point (304 in FIG. 15A) of cable passage through the assembly 506.

FIGS. 15A, 15B and 15C also illustrate the optional but useful short tensioning bands 509. The bands 509 are placed on either side of the coaster 401, with one band 509 being anchored proximate a posterior side of the glove 101, and the other band 509 extending to a controller 502. Each band 509 is connected to a pulley wheel 403.

In FIG. 15A, the anterior band 509 is shown as unattached to the glove 101; in FIG. 15B, the band 509 has been drawn forward to anchor it to the glove 101. Also visible in the views of FIGS. 15A and 15B are protective brakes 909. The brakes 909 are bonded to the rail 402. The posterior brake 909 prevents the coaster 401 from slipping backwards during elevation of the glove 101, while tension on the posterior band 509 is also keeping the coaster 401 from slipping forward. After donning is complete, the anterior band 509 can be pulled to a comfortable tension and secured to the glove 101 with a hook and loop attachment like 502 as seen in FIG. 15B. This provides a simple adjustment of the coaster's position on the rail 402. These secured bands 509 also aid in keeping the coaster 401 near the user's torso 300 during movement, and bias the coaster 401 to follow the motion of the torso 300.

The anterior brake 909 can be used to limit forward bending to a prescribed limit. Similarly the posterior brake

909 limits the extent of torso extension. Together, they provide a component for controlling bending. This may be used for protecting the wearer from exceeding a safe flexion and extension range for that wearer's physical or medical condition.

It has been shown above how the dials and related assemblies of back support device 700 (the FIG. 7 series of drawings) can be used to don, doff and adjust the device 700. This has also been shown with respect to the coaster and rail embodiments in back support devices 800, 1000, 1100, 1400 and 1500 (the FIG. 8 series of drawings, the FIG. 9 series of drawings, the FIG. 10 series of drawings, the FIG. 14 series of drawings and the FIG. 15 series of drawings). Of particular interest, in FIG. 10C the glove 101 can be seen to be raised higher on the torso 300 than in FIG. 10B. Similarly, in FIG. 15B the glove 101 can be seen to be raised higher on the torso 300 than in FIG. 10A, thus providing offloading. The glove 101 can be loosely positioned low on the torso 300 and latched. Once thus made properly proximal to the body, it can be positionally adjusted with the dials.

For an able-bodied user, combinations of dial positions are ascertained by user modeling of various positions and associating dial positions with those positions. For many mostly able-bodied users, this may be all the configuration and control desired. Here, a comfortable set of settings for control elements are captured and set for, for example, a vertical posture. Then, the back support device permits bending and twisting from this comfortable posture as needed. The posture may be set to prevent habitual bad posture, to offset or mediate unwanted spinal curvatures associated with spinal stenosis, or to minimize load on a damaged or healing part of the body.

The dial positions associated with the path between postural positions can also be similarly acquired. Thus, dial data for postural positions can be captured manually by those configuring the assembly when a desired posture is modeled. The settings for that posture are captured for later manual or powered postural acquisition which will be effected by turning the dials to those captured positions resulting in the approximately reproduced favorable effect towards a posture.

It is observed that manual adjustment mechanisms may be employed with the back support devices of the present invention. For example, elevation mechanisms that attenuate the length of medial elements may be placed in the holsters 201 (in FIG. 4B) below the medial elements. Alternatively, small, preferably ratcheted lifts like 1005 in FIGS. 10B, 10C and 10D (lever shown but pawl not visible) can replace the static holsters 201, thus allowing the user to adjust the glove's height, body posture, and the amount of offload provided to the glove 101. The elevation mechanism may be placed at the upper component 101, or, more preferably, to the lower component 102, or both. Other applicable embodiments include worm gears, pneumatics, and hydraulics for adjusting the position of, for example, the rail 402 in FIGS. 10B, 10C and 10D, support rod medial elements like 204 in FIGS. 7A and 7B, angled supports like rails 204 in FIG. 4B, and any other medial elements including the single piece 205 in FIG. 4C.

Pneumatic embodiments and some hydraulic embodiments may also include a small squeeze-bulb w/pressure-release knob (not unlike the small rubber bulb, valve assembly, and knurled release knob used to manually pump up and relieve manual blood pressure equipment) in a user's pocket with a tube leading to the actuating elements to allow wearer-directed increase or decrease of the base support pressure and thus to ramp up or attenuate support at will and while working. Other more conventional pneumatics will also be used for either manual or computer controlled adjustment of posture and position. For example, a preferred embodiment of a computer controlled assembly using these elevation controls interrogates load sensors and/or position sensors (discussed below), calculates needed changes in elevation and attitudes (including rotation), and effects these changes by boosting or attenuating element pressure and/or position.

It is also observed that the back support devices described above in their various embodiments may be modified to include powered components. Thus, a small battery may be provided, along with power wires, that enable a user to adjust the length of a medial element. In addition, such back support devices may include sensors that indicate a degree of force being placed on a medial element. Still further, such back support devices may include a transceiver that sends sensor measurements via wireless signals to a control device such as an iPhone®, an iPad® or other personal digital assistant or tablet. In this instance, a software-driven application may enable the user to adjust settings for the medial elements using the personal digital assistant or tablet.

It is noted that a substantial problem exists for paraplegics and others unable to support their bodies naturally. The current assembly provides support and good posture so that posture-exacerbated degeneration does not worsen or create a back problem. Also, by adding powered support to even the most basic embodiment, the differences in the support from different support locations can effectively control body position.

Thus, the same assembly that protects the back and helps the quadriplegic (and any weaker or older wearer) recover from injury, can, in a powered embodiment, comfortably enforce good posture, incorporate "exercise" and "airing" motions that minimize wetness, poor circulation (both air and blood) and bedsores and help prevent falls from wheelchairs, etc. caused by a leaning passenger and/or a passenger distanced from joystick or breath-straw controls.

In one embodiment, the back support devices include a processing unit having memory. Sensor readings are recorded in memory, and may be retrieved such as through a USB port or a wireless transmission of data. In this arrangement, dial positions and/or other postural indicators are captured by a sensor or a plurality of sensors associated with a processor having storage capacity to record sensor data and relate it to postures to be later acquired, favored or maintained.

The sensors may be either active or passive capture devices. Active capture devices may include actuator progress/position sensors, stepper-motors that report position or number of steps in a direction, actuated band tensioners reporting position, actuated band tensioners reporting pressure exerted, and any actuation elements reporting pressure, speed, direction or position. Thus, the dials 306, elevators like 207 in FIG. 4C when reporting at least elevation level, and the sensor-captured magnitude of loop can be referred to as active capture devices.

Passive capture devices are not necessarily rigidly tied to any particular actuation amplitude but typically by pressure exerted by an actuation element, and measures of advancement in linear and rotary actuation (e.g., mm and degrees). Bend sensors, stretch sensors, load cells, tension sensors, tensioning and/or stabilizing pulleys in the band path, etc. are all applicable sensor elements for the current invention since their duty is to report postural factors worthy of reproducing or approaching including some or all of dial positions, relative degree of flexion, extension, rotation, elevation and associated band tension at measured locations.

For example, a vertically positioned bend sensor (not shown) optionally mounted on the lower anterior of the glove intersecting the sagittal plane and extending vertically down to connect to the belt can be a good progress indicator of degree of flexion/extension used to augment or replace dial positions and other postural sensors. Bend sensors can also be placed over the spine, etc.

Cable Tension:

Dials, like 306 in FIGS. 10A, 10B, 10C, 10D and 11A, are understood to represent not only embodiments with rotational cable pickup reels but also those using any number of actuated cable retractors and dispensers known to be effective including hand-powered, powered manual and controller actuated. For some of these, the tension force on the cable is known because the amount of actuation energy invested to attain the instant tension is known and relatable to cable tension. Others may use internal or associated load cells, bend sensors and other typical means to measure forces relatable to the cable tension force. Regardless of the sensing method used to capture cable tension, that cable tension is relatable to the amount of force being offloaded.

For example, let dial 306 in FIG. 11A represent a powered retracting and dispensing actuator whose current of last actuation suggests, according to manufacturer's specifications, a tension force of, purely for example, 1 N (one Newton of force). Although in the illustration of FIG. 11A it can be seen that all of the pulley paths are not precisely vertical and although even the bearing enabled pulleys like 303 and 309 have some small amount of friction, the offload can be approximated by the pulley mechanical advantage (~8) as approximately 8 N on the side of the body thus considered. (An erect user would expect a similar amount of support on the opposite side of the wearer.) Such approximations are substantially improved with the establishment of a calibration curve based on sensor responses to known offloading forces applied in a test bed as is common practice.

Bend Sensors and Load Cells:

Bend sensors and load cells may also be used in the calculation of torso burden support/offload. For example, pulley 309 in FIG. 11A may have a shaft that rotates, and which is connected to a bend sensor. The bend sensor, in turn, measures the effects of the essentially upward pull of the cable 304 on the pulley 309. In one embodiment this can be based on the electrical conduction variations of the shaft itself responsive to the upward force, while in others it may be determined by sensors (e.g., piezoelectric) at or proximal to the mounted base of the shaft. To the extent that the vertical force upon pulley 309 is approximately the same as on the pulleys on each side, the offload for the side of the user seen in FIG. 11A is approximately three times that sensed at pulley 309. Similarly, the anchor 604 may include any bend sensor shaft (e.g., nodded normal to the glove) or load cell (e.g., positioned to measure, for example, the tension on cable 304).

Pneumatic Pressure:

Where pneumatic actuation provides the support for the offload, such as in the holsters 201, the pneumatic pressure of support is directly relatable to the total offload. For example, to the extent that an inserted end of the rail 205 is normal to the effective engagement plane of a pneumatic piston (which is itself normal to the piston's operating axis), the supportive force provided by the pneumatic cylinder being considered is equal to the pneumatic pressure sensed by the pneumatic provision system divided by the effective area of the piston, This, however, presumes that the instant pneumatic pressure is completely supporting that end of the rail and thus implementers may require that the pneumatic piston must be at least partially advanced from the zero (unextended base) position. By interrogating all of the pneumatic elements, the total offload of burden can be estimated by standard practice. Also, calibration curves, responsive to these values in coordination with bend (or other) sensors relating body position to holster loads, can be used to provide better estimates and additional values as is common practice.

Mapped Pressure-Sensitive Arrays:

Mapped pressure-sensitive arrays can also be placed between the glove 101 and the user. These can be used to measure forces on a small area or even a very large area. Any such sensors capable of measuring shear may also be used to provide a representative or relative value relatable to offload particularly when used in coordination with a calibration curve adjusting the sensor's shear value responsive to test bed testing with known offload amounts. Mapped pressure-sensitive arrays are also good indicator source data for both positions and forces. One such pressure-sensitive array is the Tekscan Model 5101 4.4"×4.4" sensor array made by Tekscan, Inc. 307 West First Street South Boston, Mass. 02127. However, any pressure sensing element, large or small or high resolution or low resolution, placed between the contact areas of the current invention and the wearer or similarly located for measurement of these forces are applicable to the current invention.

An optional embodiment includes such a pressure map or a plurality of individual sensors inside the glove to capture and send to the processor indications of what pressures are being exerted against the glove from the body inside. Thus, for example, the controlling software running on the processor can respond to, for example, pressures under the armpits being heavier than normal (normal here being values found to be normal for an erect user) on the right side and less than normal on the left as an indication of both degree of lean to the right and user comfort level during the activity. High values from pressure sensors in the lower anterior edge of the glove are directly applicable to recognizing a relative degree of flexion/extension (the higher the value, presuming adequate vertical offload as is normal, in the front and the lower pressure readings at the bottom in the back, the greater the relative flexion. This is approximate but it can be calibrated to the user's body at configuration time or even during action by well understood calibration curve processes.

Behavior Capture:

In connection with the use of the back support devices described above, it may be desirable to capture data during use. This is done through sensed postural indicators. When a user needs help assuming or maintaining a certain postural position, the user may indicate, using any user human machine interface (HMI) convenient for that user, to the processor a desired postural position (e.g., a degree of trunk flexion desired communicated digitally, graphically, orally or by any practical HMI input). During prior training, the user wearing the assembly or a similar assembly moved (or was moved) from, for example, an erect position to the maximum extent of flexion possible for the equipment and the user preferably at a desirable speed of flexion or a speed proportionate to a desired speed of flexion.

As this action progresses the processor captures the sensor values (sensor here including all indicators mentioned herein and others with obviously similar functions) associated with each point achieved in the process of flexion and then back to erect. Thus, for example, all the anterior (and/or posterior)

bend sensor values at each fraction of a degree of flexion/extension are known. Thus, for the processor to respond to that user requested degree of flexion from any current degree of flexion only requires that the processor direct flexion actuation, e.g., loosening the anterior dials, 306, and tightening the posterior dials, until the bend sensor value for the requested degree of flexion is achieved. For lateral bend sensors vertically aligned and attached to the bottom of the glove at the left and right side of the glove extending downward towards, to or past the belt, a modeled bend sensor value array can be similarly captured as the user leans left or right.

Again, to respond to an HMI request for a degree of lean to, say, the right, requires only that the processor recognize the current approximate degree of lean (which may be negative, like an azimuth value left of zero, if the subject is currently leaning to the left), direct a lean motion in the requested direction, left or right, (e.g., tightening, i.e. turning the left side dials, 306 in FIGS. 7A and 7B or FIGS. 10B, 10C and 10D clockwise and or loosening the bands on the right side to lean more rightward) until the lateral bend sensors return a reading to the processor essentially equal to the value of those sensors when the subject or a model was leaned to that desired angle. Also, the progress of that change can proceed at the same or a proportional speed to that of the training session modeling session.

If there are enough bend sensors and/or other sensors to recognize and report progress in flexion/extension and left/right leaning, the same processor can direct and monitor the progress of a commanded lean in any direction, e.g., leaning towards an azimuth of 40 degrees (essentially leaning forward and to the right). There are numerous applicable methods for ascertaining the various potentially simultaneous adjustments required for performing this on the assembly of the current invention but the preferred method will now be described. The passive values, including but not limited to the bend sensors described above, load cells, translational displacement sensors and pressure maps, are primarily used to determine or confirm (potentially along with other values) a current position or posture, recognize progress (and rate of progress) towards the goal, and when to stop as in an ordinary closed loop system. Passive values are all that is needed for simple or specifically programmed operations.

The dials 306 are understood to represent any actuated or manual element for the control of a band 304. However, at least the assembly used for modeling an action (e.g., leaning forward and to the right, 40 degrees pitch and 30 degrees yaw from an erect, 0 azimuth stance) possesses the ability to capture active values (values that effect postural change). A few examples of values "reflective of a dial setting" are active values (whose amplitudes effect change) like actuator settings and passive elements like bend sensors, translational displacement sensors, pressure maps and load cells.

Because both of these also slightly induce flexion, simultaneous countering (offsetting) anti-flexion adjustments can be made such as tightening slightly the two anterior dials 306, in FIG. 7A and/or loosening the rear dials on both left and right sides to offset the twist-induced flexion and achieve a net desired rotation. These preferably simultaneous operations are best accomplished with a computer controlled actuation of the dials.

In one embodiment, dual front and rear dials, cables and anchor assemblies are the only active actuating elements in use. In this instance, to rotate the user's body counterclockwise, the left anterior dial is tightened, the left posterior dial is loosened, the right anterior dial is loosened and the right posterior dial is tightened. Clockwise rotation involves a reversal of those. Flexion is favored by tightening the two anterior dials and loosening the two posterior dials. Extension involves a reversal of those.

Again, with these disclosed, fractional combinations of different dial controls as well as associated and optionally additive countering/offsetting elements from elevation controls to counter or assist elements, the numerous possible combinations of controls thus provided and described to effect any given positional and/or load-offload response will be understood.

In other embodiments, these dials will be replaced where desirable with the familiar ratcheting wheel or lever assemblies and other components that are also used to retract and release cable/bands. The dials 306, are simply shown as one of many applicable types of take-up element. In an actuated band take-up embodiment, these dials illustrated are then alternatively seen as (understood to be) powered take-up reels or other take-up actuated elements. In the preferred motorized embodiment, these powered take up elements return at least positional information to a computer controller enabling the controller to manage either or both posture and offload adjustment. As will be described further below, some of these will also return sensor information driven by the tension on the band which can, particularly with positional data available, be calibration-curve related to how much relief and protection from overload is being provided.

"Heavy Lifting" (Auxiliary Support):

For users in need of more significant amounts of positional assistance, the "heavy lifting" of such assistance is optionally provided by additive corollary (and preferably passive) medial elements, thus reducing the amount of adjustment force required by adjustment elements. Just as one of many applicable examples of combinations of medial elements and other devices, a subject with tetraplegia tends to flex/slump forward in a wheelchair. By placing extension favoring medial elements like rods 204 in FIG. 4A (which just takes bending a thin carbon rod and placing ends in the holsters 201) on each side (1 left, 1 right side), flexion/slumping is resisted. Then, with the maximum amount of force exertion thus minimized, powered adjustment elements such as those discussed above and below can be used with less powerful actuator components that are also less expensive, lighter, produce less heat, and are easier to conceal under ordinary clothing.

Thus, by controlling these few low-overhead and multi-purpose control elements, all of the adjustment facilities are provided to easily don and doff the assembly, adjust support with favorable leverage, position the subject in almost any complex position while continuously maintaining support, even during said adjustments and changes, in a favorable direction at a favorable mechanical advantage and with reverse-leverage-enhanced throw distance.

One preferred automated embodiment for automated positional adjustment includes a computer controller with a closed-loop control system for acquiring a desired set of posture goals), sampling any disparity between a goal and current positions, and adjusting the goal in real time. In connection with this embodiment, load can be monitored (or calculated/approximated as the simple net of known torso weight and sensed offload amount) and the user warned through any HMI when an unsafe or undesirable condition exists. For example, an audio warning (ranging from a beep to a voice simulated message) can warn the user when positional sensing indicates poor posture (e.g., an excessive flexion over an extended time indicative of a slump associated with exacerbation of back problems and bedsores on seated wearers). Similarly, the user can be alerted when a pressure sensor worn between the glove and the body indicates pressures associated with excessive vascular constriction (which can be, at some body locations and for extended periods of wear, just a few PSI).

Some users may be unable to make real-time adjustments, while others may prefer to have some orthosis adjustments made for them. Thus, using the actuator enabled adjustments discussed above, the back support device can be programmed for correcting behavior, reporting wearer compliance and correcting problems with adjusted support.

For example, the onboard actuator processor and controller 408 of FIG. 11A is connected by wire to the actuating dial 306, receives offload data from a sensor at pulley 309, and receives power for itself and for the actuator 408 from battery 900 which is connected to the belt 103. In the preferred embodiment the onboard actuator processor and controller 408 is wirelessly connected to a laptop computer, a smart phone application or other HMI where preferences are kept. When, for example, the offload value sensed by sensor 309 is less than the offload minimum preference mediated by 408 (perhaps the glove has slipped slightly on the wearer's body), the actuator 306 is powered and directed by 408 to retract cable until the sensor 309 reports and offload value adequately close to the minimum preference value. Reversing the process or reduced offload as well is applying this approach to any and all dials and other actuating elements to control even complex computer aided postural adjustment by adjusting the various dials (as described in detail above) is also possible.

What is claimed is:

1. A back support device for supporting a portion of a burden otherwise borne by a user's spinal column and abdomen, comprising:
   a compliant upper support component configured to be radially worn around at least part of an upper torso of the user and under arms of the user, the upper component comprising a network of fingers for snugly engaging the torso; and
   a separate compliant lower component configured to be snugly worn at least partially around hips and waistline of the user; and
   wherein the network of fingers comprises (i) a series of through-openings oriented along and configured to engage tissue and ribs of the user to provide stability of the upper component along the user's torso, (ii) areas of increased thickness along the upper component, (iii) areas of increased stiffness along the upper components, and (iv) combinations thereof.

2. The back support device of claim 1, further comprising:
   a plurality of medial elements connected to the upper and lower support components, with the medial elements configured to support the portion of the burden by transferring the burden from the upper component to the lower component, thereby relieving spinal compression.

3. The back support device of claim 2, wherein the medial elements attach to the upper support component at the areas of increased material thickness, at the areas of increased material stiffness, or both, of the upper support component.

4. The back support device of claim 2, wherein:
   at least two of the medial elements comprise flexible rods, with at least one rod being placed proximate a posterior side of the user's torso, and an arcuate rod being placed on an anterior side of the user's torso; and
   the arcuate rod placed on the anterior side comprises a continuous rail having opposing ends and an apex therebetween, with each end being anchored in the lower support component and the apex being operatively connected to the upper support component.

5. The back support device of claim 2, wherein the upper support component comprises an inner surface having a plurality of raised horizontal ridges that form at least a part of the network of fingers.

6. The back support device of claim 2, wherein:
   the plurality of medial elements comprises at least four flexible rods spaced radially around the user, each rod having a first end and a second end, with the first end of each rod connected to the upper component and the second end connected to the lower component; and
   each of the flexible rods is resiliently bent between the upper and lower support components to provide spinal distraction while the back support device is worn by the user.

7. The back support device of claim 6, wherein each of the flexible rods comprises a bundle of two or more flexible rods.

8. The back support device of claim 2, wherein the plurality of medial elements comprises a pair of flexible rods, with each rod having a first rod end and a second rod end, and with each rod being placed on opposing left and right sides of the user for providing spinal distraction.

9. The back support device of claim 8, wherein:
   the second rod end of each of the pair of rods is connected to the lower component; and
   the first rod end of each of the pair of rods is connected to a plate, with the plate comprising a plurality of pulleys, and with each of the pulleys being connected to the upper support component by at least one elastic tensioning band, wherein adjusting the tension of the tensioning bands adjusts the position of the plate relative to the upper support component and the degree of spinal distraction.

10. The back support device of claim 9, wherein:
    each tensioning band possesses a first band end connected to the upper component, and a second band end connected to a tensioning dial along the lower component; and
    rotation of each tensioning dial adjusts the tension in the corresponding band, thereby adjusting a degree of load transferred from the upper support component to the lower support component.

11. The back support device of claim 10, wherein:
    the at least one elastic tensioning band comprises a pair of bands on each side of the user, with the first band end of each pair of bands being secured to the upper component at opposing sides of the rod; and
    the second band ends of each pair of bands and the corresponding tensioning dials are configured such that (i) turning both dials on a side of the user in a first rotational motion in coordination with each other increases the potential for flexion in the user's torso, and (ii) turning both dials on a side of a user in a second opposite rotational motion in coordination with each other increases the potential for extension in the user's torso.

12. The back support device of claim 8, wherein:
    each of the flexible rods comprises an arcuate rail, wherein the opposing first and second rod ends of each arcuate rail is anchored to the lower support component, thereby forming an apex between the first and second rod ends; and
    the back support device further comprises a pair of coasters, with each coaster being operatively connected to the upper support component on opposing sides of the user, the coasters being configured to receive and ride along the apex of the respective rails.

13. The back support device of claim 8, wherein:
each of the flexible rods comprises an arcuate rail, wherein the opposing first and second rod ends of each arcuate rail are anchored to the upper support component, thereby forming an apex between the first and second rod ends; and
the back support device further comprises:
  body guides affixed along the lower support component and defining tabs configured to receive a respective rail and to limit movement of the rails relative to the lower support component;
  a pair of coasters, with each coaster being operatively connected to the lower support component on opposing side. of the user, the coasters being configured to receive and ride along the apex of the respective rails; and
  a plurality of rollers affixed to each of the coasters, wherein the rollers are spaced and dimensioned along the respective coasters to receive and guide the apexes of the respective rails during movement of the user.

14. The back support device of claim 2, wherein the plurality of medial elements comprises:
  a pair of substantially rigid rods, with each rod having a first rod end and a second rod end, and with each rod being placed along the abdomen of the user;
  a pair of upper holsters for receiving the first rod end of respective rods along the upper support component; and
  a pair of lower holsters for receiving the second rod end of the respective rods along the lower support component.

15. The back support device of claim 14 wherein the upper holster comprises a bore for slidably receiving an upper end of each of the respective rods, thereby permitting limited travel of the rods within respective upper holsters.

16. The back support device of claim 15, wherein the bore of each upper holster comprises an elastomeric or a foam material for cushioning movement of the upper end of each of the respective rods within the corresponding bore.

17. A back support device for supporting a portion of a burden otherwise borne by a user's spinal column and abdomen, comprising:
  a compliant upper support component configured to be radially and snugly worn around at least part of an upper torso of the user and under arms of the user;
  a separate lower support component configured to be snugly worn at least partially around hips and waistline of the user;
  a pair of arcuate, flexible rails positioned between and operatively connected to each of the upper and lower support components, with a rail being placed on each side of the user under the user's arms, wherein each of the rails is configured to support the portion of the burden by transferring the burden from the upper component to the lower component; and
  a coaster operatively connected to the upper component under each of the user's arms, each coaster configured to translate along an arch of each of the rails, thereby facilitating mobility of the user.

18. The back support device of claim 17, wherein:
each of the flexible rails comprises opposing first and second rod ends, with each of the first and second ends being anchored to the lower support component, thereby forming an apex between the first and second rod ends, and with the apex of each rail generally residing under a respective arm of the user; and
each of the coasters comprises at least one roller configured to translate along the arches of the respective rails during movement of the user.

19. The back support device of claim 18, wherein:
the at least one roller of each of the coasters comprises at least two rollers, with the rollers being spaced and dimensioned along the coasters to receive the arches of the respective rails; and
the back support device further comprises body guides affixed along the upper support components on each side of the user, the body guides defining tabs configured to receive the respective rails and to limit movement of the rails relative to the upper support component.

20. The back support device of claim 19, further comprising:
  a first brake secured along each of the rails on a first side of the respective coaster, and a second brake secured along each of the rails on a second opposite side of the respective coaster, wherein the brakes serve as limits to the degree of forward and backward mobility of the user's torso.

21. The back support device of claim 18, wherein the elevation of the apex of at least one of the rails is vertically adjustable relative to the lower support component, thereby allowing a selective increase or decrease of the burden carried by the rails.

22. The back support device of claim 21, wherein the change in elevation of the apex of the at least one of the rails is accomplished by increasing the length of a portion of the rail between the points of attachment to the lower support component and the coaster.

23. The back support device of claim 22, further comprising:
  a length adjusting mechanism for adjusting the length of at least one of the rails, the mechanism comprising at least one ratcheting mechanism, a pneumatic lift mechanism, or a hydraulic lift mechanism provided along the lower support component.

24. The back support device of claim 18, further comprising:
  a loop selectively placed around opposing sides of each of the opposing rails, wherein the loop is positioned below the apex and serves to selectively modify the curvature and supportive nature of the respective rail and to limit flexibility of the respective rail relative to a corresponding coaster.

25. The back support device of claim 24, wherein the curvature of the rails is adjusted by adjusting the length of the loop around the rail such that tightening loop generally increases the stiffness of the arch, while loosening the loop generally decreases the stiffness of the arch.

26. The back support device of claim 21, wherein a change in elevation of the apex of the rails is accomplished by configuring each coaster to be slideably attached to the upper component, whereby each coaster is able to vertically translate relative to the upper component.

27. The back support device of claim 26, further comprising:
  a plurality of cables and pulleys which limit the vertical movement of the coasters, wherein the selective tensioning of the cables allows the user to increase the portion of the burden borne by the lower support component.

28. The back support device of claim 22, wherein the lower support component comprises points of increased stiffness at areas where the first and second rod ends are anchored.

29. The back support device of claim 17, wherein
the upper component comprises a network of fingers for engaging the torso, the network of fingers comprising (i) a series of through-openings oriented along and configured to engage ribs of the user to provide stability of the upper component along the user's torso, (ii) areas of increased thickness along the upper component, (iii) areas of increased stiffness along the upper components, and (iv) combinations thereof.

30. A back support device for supporting a portion of a burden otherwise borne by a user's back, comprising:
a compliant upper support component configured to be radially and snugly worn around at least part of an upper torso of the user under the user's arms;
a compliant lower component configured to be snugly worn at least partially around hips and waistline of the user;
a plurality of flexible rods connected to each of the upper and lower components, with the rods being configured to support the portion of the burden by transferring the burden from the upper component to the lower component; and
a plurality of holsters provided along the lower component wherein each of the plurality of holsters is configured to receive a respective end of a flexible rod, and to provide resistance to pivoting of the rod so as to provide postural support to the back of the user.

31. The back support device of claim 30, wherein each of the holsters rigidly secures an end of one of the flexible rods.

32. The back support device of claim 30, wherein each of the holsters is constructed from a compliant material supported by a rigid material, with each holster comprising:
an outer shell comprised of a rigid material; and
an inner portion, surrounded by the outer shell, comprised of a resilient compliant material;
wherein each of the respective rod ends s positioned within and extends from the inner portion, thereby allowing bending of the portion of the rod end embedded within the inner portion.

33. The back support device of claim 30, wherein each of the holsters is secured to the lower component by means of a pivoting connection.

34. The back support device of claim 30, wherein
the upper component comprises a network of fingers for engaging the torso, the network of fingers comprising (i) a series of through-openings oriented along and configured to engage ribs of the user to provide stability of the upper component along the user's torso, (ii) areas of increased thickness along the upper component, (iii) areas of increased stiffness along the upper components, and (iv) combinations thereof.

* * * * *